(12) United States Patent
Kong et al.

(10) Patent No.: US 9,677,063 B2
(45) Date of Patent: Jun. 13, 2017

(54) USE OF A CYSTEINE PROTEASE OF PLASMODIUM VIVAX

(71) Applicant: SAMSUNG ELECTRONICS CO., LTD., Suwon-si (KR)

(72) Inventors: Yoon Kong, Seoul (KR); Byoung-Kuk Na, Jinju-si (KR); Seon-Hee Kim, Suwon-si (KR); Young-An Bae, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 273 days.

(21) Appl. No.: 14/321,952

(22) Filed: Jul. 2, 2014

(65) Prior Publication Data

US 2014/0370570 A1 Dec. 18, 2014

Related U.S. Application Data

(63) Continuation of application No. 12/861,918, filed on Aug. 24, 2010, now abandoned.

(60) Provisional application No. 61/236,198, filed on Aug. 24, 2009.

(51) Int. Cl.

| | |
|---|---|
| *C12Q 1/00* | (2006.01) |
| *C12Q 1/37* | (2006.01) |
| *A61K 38/48* | (2006.01) |
| *C12N 9/50* | (2006.01) |
| *C12N 9/64* | (2006.01) |
| *C12Q 1/18* | (2006.01) |

(52) U.S. Cl.
CPC ............. *C12N 9/50* (2013.01); *A61K 38/4873* (2013.01); *C12N 9/6475* (2013.01); *C12Q 1/18* (2013.01); *C12Q 1/37* (2013.01); *C12Y 304/22* (2013.01); *G01N 2333/445* (2013.01); *G01N 2333/8139* (2013.01); *G01N 2333/96469* (2013.01)

(58) Field of Classification Search
CPC .... A61K 38/4873; C12N 9/50; C12N 9/6475; C12Q 1/37; C12Y 304/22; G01N 2333/445; G01N 2333/8139; G01N 2333/96469
USPC ......... 435/23; 424/272.1; 514/20.2; 530/350
See application file for complete search history.

(56) References Cited

U.S. PATENT DOCUMENTS

2004/0106805 A1 6/2004 Quibell et al.

OTHER PUBLICATIONS

Ajay Singh et al., Selection of cysteine-protease inhibitor-resistant malaria parasites is accompanied by amplification of falcipain genes and alteration in inhibitor transcript, The Journal of Biological Chemistry, Aug. 20, 2004, vol. 279, pp. 35236-35241.
Byoung-Kuk Na et al., Biochemical properties of a novel cysteine protease of Plasmodium vivax, vivapain-4, Oct. 12, 2010, PLOS, vol. 4, e849, 10 pages.
Na et al., Characterization of vivapain-4, the fourth cysteine protease of Plasmodium vivax, UniProt entry, SCORE report, 2004, 3 pages.
Byoung-Kuk Na et al., Identification and biochemical characterization of vivapains, cysteine proteases of the malaria parasite Plasmodium vivax, Biochemical Journal, Mar 1, 2004, vol. 378, pp. 529-538.
Estefan Miranda-Miranda et al., Expression of a Haemonchous contorus cysteine protease in the baculovirus system, 2008, Electronic Journal of Biotechnology, Apr. 15, 2008, pp. 1-7, vol. 11, No. 2.

*Primary Examiner* — Sharmila G. Landau
*Assistant Examiner* — Shannon Janssen
(74) *Attorney, Agent, or Firm* — Lex IP Meister, PLLC

(57) ABSTRACT

A use of vivapain-4 (VX-4), which is a cysteine protease of *Plasmodium vivax*, showing pH-dependent switching of substrate specificity, is provided. More specifically, a method of treating a parasitic disease caused by *Plasmodium vivax* by inhibiting VX-4; a method of screening a protease inhibitor acting on VX-4, wherein the protease inhibitor is useful as an anti-malarial agent acting on *Plasmodium* species, for example, *Plasmodium vivax*; and a method of identifying the activity of VX-4, are provided.

8 Claims, 7 Drawing Sheets

Fig. 1A

USE OF A CYSTEINE PROTEASE OF PLASMODIUM VIVAX

This application is a Continuation Application of U.S. patent application Ser. No. 12/861,918, filed Aug. 24, 2010, which claims priority to and the benefit of U.S. Provisional Application No. 61/236,198, filed Aug. 24, 2009, which is incorporated by reference herein in its entirety for any purpose.

BACKGROUND OF THE INVENTION

The present invention relates to vivapain-4 (VX-4), which is a cysteine protease of *Plasmodium vivax*, showing pH-dependent switching of substrate specificity. More specifically, the present invention relates to a method of treating a parasitic disease caused by *Plasmodium vivax* by inhibiting VX-4, a method of screening a protease inhibitor acting on VX-4, wherein the protease inhibitor is useful as an antimalarial agent acting on *Plasmodium* species, for example, *Plasmodium vivax*, and a method of identifying the activity of VX-4.

DESCRIPTION OF RELATED ART

*Plasmodium vivax*, one of the most predominant human malarial species worldwide, causes hundreds of millions of illnesses each year, and can result in severe morbidity and mortality. Emergence and spread of multidrug resistant vivax malaria is an increasing problem, and is associated with fatal disease, especially in children.

Cysteine proteases of malaria parasites are intimately involved in a variety of physiological processes essential for the parasite's survival. The potential biological significance of the cysteine proteases of *P. falciparum* such as falcipain-2 (FP-2), -2B (-2') and -3 in conversion of precursor molecules into mature active proteins and erythrocytic rupture via cleavage of cytoskeletal proteins followed by merozoite release has been well characterized. Their independent roles in hemoglobin digestion in the food vacuole and coordinated function with other proteases in regulation of hemoglobin hydrolysis have been elucidated. These three FP-encoding genes cluster on chromosome 11 within a narrow 12-kb stretch, called the cysteine protease island. Another papain-like cysteine protease, FP-1, is located on chromosome 14. It is expressed in the asexual stage and is involved in oocyst production in mosquitoes and in the early invasive merozoite stage.

Two cysteine proteases, vivapain-2 (VX-2) and vivapain-3 (VX-3), have been identified in *P. vivax*. The VX-2 and VX-3 genes are located on chromosome 9, and the proteins share a number of biophysical and biochemical features with FP-2 and FP-3, including a long prodomain with a predicted short N-terminal extension, acidic pH optima, and requirement for reducing conditions for maximal enzyme activity. Structural analysis of VX-2 and VX-3 proteins has revealed a topology similar to those of FP-2 and -3; however, some critical differences exist between the sizes of the binding pockets and amino acid (AA) binding preferences, which include the preference for positively charged residues at P1 and Leu at P2 position. A gene (XM_001612308) showing a significant similarity to FP-1 has recently become available in the nucleotide sequence of *P. vivax* chromosome 12 in the GenBank database (PVX_195290, PVX_240290 and PVX_239290), while its biochemical properties and biological activity remain unclear.

Interests in specific inhibitors impeding the cysteine protease functions of *P. falciparum* and *P. vivax* have focused on their chemotherapeutic applicability, which might impair normal parasite growth in vitro. For example, rupture of the erythrocyte membrane by the invasive parasite is inhibited by broad-spectrum inhibitors of serine and cysteine proteases. Identification and further characterization of *P. vivax* cysteine proteases is essential not only to investigate their biological roles but also to characterize targets for antimalarial drugs. However, comprehensive studies of *P. vivax* cysteine proteases have been highly hindered mainly due to the inability to culture *P. vivax*.

SUMMARY OF THE INVENTION

One embodiment provides a method of treating a parasitic disease caused by *Plasmodium vivax*, by administering an inhibitor against *Plasmodium vivax* cysteine protease (VX-4, AAT91956, SEQ ID NO: 1) to a patient in need of the parasitic disease treatment, wherein the inhibitor is capable of inhibiting the expression of glutamic acid at $180^{th}$ position (Glu180) in VX-4, or substituting the Glu180 with an amino acid other than glutamate, or inactivating the Glu180, wherein the number of the amino acid position is initiated from the mature domain (SEQ ID NO: 2) of VX-4.

Another embodiment provides a method of screening an inhibitor against VX-4 or an anti-malarial agent against *Plasmodium vivax* using glutamic acid at $180^{th}$ position (Glu180) in VX-4 as a target.

Another embodiment provides a method of screening an inhibitor against VX-4 or an anti-malarial agent against *Plasmodium vivax* using a pH-dependent substrate specificity of VX-4.

Still another embodiment provides a method of identifying the activity of VX-4 by examining a pH-dependent substrate specificity of VX-4.

These and other embodiments of the invention will be more fully understood from the following description of the invention and the claims appended hereto.

DETAILED DESCRIPTION OF THE EMBODIMENT

The inventors isolated and identified a novel cysteine protease of *P. vivax*, designated as vivapain-4 (VX-4, AAT91956, SEQ ID NO: 1), which displays highly unusual pH-dependent substrate specificity, and characterized the biochemical properties of VX-4. Molecular modeling and subsequent mutation analysis of VX-4 demonstrated that Glu180 is involved in the pH-dependent substrate specificity of VX-4. The protease is localized in the cytoplasm of the whole erythrocytic stages of the parasite. It effectively hydrolyzes actin at neutral pH (e.g., pH 6.8 to 7.2, preferably approximately pH 7) and plasmepsin 4 at neutral and acidic pHs (e.g., pH 5-7), supporting its role in the maintenance of cellular homeostasis and architectural remodeling of the parasite during development.

*Plasmodium vivax* affects hundreds of millions each year and results in severe morbidity and mortality. Plasmodial cysteine proteases (CPs) play crucial roles during the progression of malaria since inhibition of these molecules impairs parasite growth. These CPs might targeted for new antimalarial drugs. The inventors herein characterized a novel *P. vivax* CP (VX-4), which appeared to evolve differentially among primate *Plasmodium* species. VX-4 showed highly unique substrate preference depending on surrounding micro-environmental pH. It effectively hydrolyzed benzyloxycarbonyl-Leu-Arg-4-methyl-coumaryl-7-amide (Z-Leu-Arg-MCA) and Z-Phe-Arg-MCA at acidic pH and Z-Arg-Arg-MCA at neutral pH. Three amino acids (Ala90, Gly157 and Glu180) that delineate the S2 pocket were found to be substituted in VX-4. Hereinafter, the amino acid positions of Ala90, Gly157 and Glu180 are numbered from the mature domain of VX-4, and the mature domain (SEQ ID NO: 1) of VX-4 and the initial peptide thereof are shown in FIGS. 1A and 1B. Alteration of Glu180 abolished activity against Z-Arg-Arg-MCA at neutral pH, indicating the importance of Glu180 in the pH-dependent substrate preference. VX-4 hydrolyzed actin at neutral pH and hemoglobin at acidic pH, and participated in plasmepsin IV activation at neutral/acidic pH. VX-4 was localized in the food vacuoles and cytoplasm of the erythrocytic stage of *P. vivax*. The differential substrate preferences depending on pH suggested a highly efficient mechanism to enlarge biological implications of VX-4, including hemoglobin degradation, maturation of plasmepsin, and remodeling of the parasite architecture during growth and development of *P. vivax*.

Based on the above study, the present invention was completed. The present invention will be described in detail as below.

Definitions

For convenience, certain terms employed in the specification, examples, and appended claims are collected here.

It is to be understood that this invention is not limited to the particular methodology, protocols, animal species or genera, and reagents described, as such may vary. It is also to be understood that the terminology used herein is for the purpose of describing particular embodiments only, and is not intended to limit the scope of the present invention that will be limited only by the appended claims.

Therefore, the term "a patient in need of treatment" as used herein will refer to any subject or patient who currently has or may develop any of parasitic diseases caused by *P. vivax*.

The term "treating" or "treatment" as used herein, refers to any indicia of success in the prevention or amelioration of pathology or condition of the parasitic diseases caused by *P. vivax*, or making the pathology or condition more tolerable to the patient, or improving a subject's physical or mental well-being. In some instances, treatment with the agent of the present invention will be done in combination with other agent to prevent, inhibit, or arrest the progression of the parasitic diseases.

The term "therapeutic effect" as used herein, refers to the effective improvement in or reduction of symptoms of parasitic diseases. The term "a therapeutically effective amount" as used herein means a sufficient amount of one or more of the compounds of the invention to produce a therapeutic effect, as defined above, in a subject or patient in need of such parasitic disease treatment.

The terms "subject" or "patient" are used herein interchangeably and as used herein mean any mammal including but not limited to human beings including a human patient or subject to which the compositions of the invention can be administered. The term mammals include human patients, both male and female and non-human primates, as well as experimental animals such as rodent (e.g., rabbits, rats, mice, and the like) and other animals.

The term "degrading activity" includes all enzymatic activity of cysteine protease, such as a hydrolytic activity, cleavage activity, and the like.

The terms "vivapain-4" and "VX-4" are used herein interchangeably, and include a recombinant vivapain-4 expressed from a recombinant expression vector comprising vivapain-4 coding polynucleotide as well as a vivapain-4 obtained from *P. vivax*. They may include a mature domain, or a whole or part of prodomain in addition to the mature domain (see FIGS. 1A and 1B).

As described above, isolated and identified a novel cysteine protease of *P. vivax,* designated as vivapain-4 (VX-4) (AAT91956, SEQ ID NO: 1) was isolated and identified. Therefore, an aspect of the present invention relates to vivapain-4 (VX-4) (AAT91956, SEQ ID NO: 1). The protein is characterized its unique function as described below and the position of amino acid residues lining the binding pockets (S2 pocket) as shown in FIG. 5(B).

VX-4 was characterized and its orthologs appears to have evolved differentially in primate plasmodia with strong cladistic affinity toward those of rodent *Plasmodium*. As shown in the following examples, a recombinant VX-4 demonstrated dual substrate specificity depending on the surrounding micro-environmental pH. Its hydrolyzing activity against benzyloxycarbonyl-Leu-Arg-4-methyl-coumaryl-7-amide (Z-Leu-Arg-MCA) and Z-Phe-Arg-MCA was highest at acidic pH (e.g., pH 4.5 to lower than 6.5, preferably approximately pH 5.5), whereas that against Z-Arg-Arg-MCA was maximal at neutral/alkaline pH (e.g., pH 6.5 to 9, preferably pH 6.5-7.5).

The molecular substrates, such as dipeptidyl substrates having at least one hydrophobic amino acid (e.g., Z-Leu-Arg-MCA and Z-Phe-Arg-MCA), are favored by cathepsin L; whereas the molecular substrates, such as dipeptidyl substrates at least one hydrophilic amino acid (e.g., Z-Arg-Arg-MCA) are favored by cathepsin B. The VX-4 exhibits both of activities of a cathepsin L and cathepsin B depending on pH, that is, VX-4 exhibits cathepsin L activity at acidic pH (e.g., pH 4.5 to lower than 6.5, preferably approximately pH 5.5), and cathepsin B activity at neutral/alkaline pH (e.g., pH 6.5 to 9, preferably pH 6.5-7.5).

VX-4 preferred positively charged amino acids and Gln at the P1 position, with less strict specificity at P3 and P4. P2 preferences depended on pH (Leu at pH 5 to 6, preferably approximately pH 5.5 and Arg at pH 7 to 8, preferably approximately pH pH 7.5). Three amino acids that delineate the S2 pocket were substituted in VX-4 compared to VX-2/VX-3 (Ala90, Gly157 and Glu180). Replacement of Glu180 abolished activity against Z-Arg-Arg-MCA at neutral pH, indicating the importance of this amino acid in the pH-dependent substrate preference. VX-4 was localized in the food vacuoles and cytoplasm of the erythrocytic stage of *P. vivax*. VX-4 showed maximal activity against actin at neutral pH (e.g., pH 6.8 to 7.2, preferably approximately pH 7), and that against *P. vivax* plasmepsin 4 and hemoglobin was detected at neutral/acidic pH (e.g., pH 5-7) and acidic pH (e.g., pH 5.5 to 6), respectively.

Based on the above study, another aspect of the present invention relates to a method of identifying the activity of VX-4 (AAT91956, SEQ ID NO: 1) comprising at least one step of:

(a) the degrading activity of the vivapain-4 or the expressed vivapain-4 from the recombinant expression vector against a dipeptidyl substrate favored by cathepsin L at pH 4.5 to 6.5, preferably approximately pH 5.5, wherein the dipeptidyl substrate has at least one hydrophobic amino acid;

(b) the degrading activity of the vivapain-4 or the expressed vivapain-4 from the recombinant expression vector against a dipeptidyl substrate favored by cathepsin B at pH 6.6 to 9, preferably pH 6.6 to 7.5, wherein the dipeptidyl substrate has at least one hydrophilic amino acid;

(c) the degrading activity of the VX-4 or the expressed vivapain-4 from the recombinant expression vector against actin at neutral pH, such as pH 6.8 to 7.2, preferably approximately pH 7;

(d) the degrading activity of the VX-4 or the expressed vivapain-4 from the recombinant expression vector against hemoglobin at acidic pH such as pH 5.5 to 6; and (e) the cleavage activity of the VX-4 against plasmepsin at neutral/acidic pH, such as pH 5-7, and (f) identifying the presence of glutamic acid at $180^{th}$ position (Glu180) in VX-4, wherein the number of the amino acid position is initiated from the mature domain (SEQ ID NO: 2) of VX-4 (the initial amino acid of the mature domain (SEQ ID NO: 2) of VX-4 is represented with a shading mark in FIG. 1B).

The hydrophobic amino acid of (a) may selected from the group consisting of alanine, isoleucine, leucine, methionine, phenylalanine, proline, tryptophane, valine, cysteine, and the like. In the concrete embodiment of the present invention, benzyloxycarbonyl-L-phenylalanyl-L-arginine 4-methyl-coumaryl-7-amide (Z-Phe-Arg-MCA) or benzyloxycarbonyl-leucyl-L-arginine 4-methyl-coumaryl-7-amide (Z-Leu-Arg-MCA) is used as the dipeptidyl substrate of (a).

The hydrophilic amino acid of (b) is selected from aspartic acid, glutamic acid, arginine, histidine, and lysine. In the concrete embodiment of the present invention, benzyloxycarbonyl-L-arginyl-L-arginine 4-methyl-coumaryl-7-amide (Z-RR-MCA) is used as a dipeptidyl substrate of (b).

As described above, glutamic acid at $180^{th}$ position (Glu180) in VX-4 plays an important role in the pH-dependent substrate specificity, and thus, the Glu180 may be useful in developing an agent for preventing and/or treating a parasitic disease caused by *Plasmodium vivax*, such as malaria.

Therefore, another aspect of the present invention relates to a method of screening an anti-malarial agent against *Plasmodium vivax* comprising:

providing *Plasmodium vivax* cysteine protease (VX-4, AAT91956, SEQ ID NO: 1) or an expression vector comprising a polynucleotide encoding the VX-4;

contacting the VX-4 with a candidate material or culturing the recombinant expression vector with a candidate material; and examining glutamic acid at $180^{th}$ position (Glu180) in VX-4 or the expressed VX-4, wherein the number of the amino acid position is initiated from the mature domain (SEQ ID NO: 2) of VX-4.

In this method, the candidate material is determined as the anti-malarial agent against *Plasmodium vivax*, when Glu180 is deleted, substituted with an amino acid other than glutamate, or inactivated, in the VX-4 or the expressed vivapain-4 from the recombinant expression vector. The amino acid other than glutamate may be a basic or hydrophobic amino acid. The amino acid other than glutamate is an amino acid selected from the group consisting of arginine, histidine, lysine, alanine, isoleucine, leucine, methionine, phenylalanine, proline, tryptophane, valine, cysteine, and the like.

The candidate material may be any compounds, including synthetic or natural compound.

The recombinant expression vector comprising a polynucleotide encoding the VX-4 may be constructed and cultured according to any conventional method. The recombinant expression vector may be cultured in an appropriate host cell, such as *E. coli*, but not limited thereto.

The deletion and substitution of Glu180 in VX-4 may be examined by any conventional peptide or protein analysis method, such as amino acid sequencing.

In another aspect, the present invention relates to a novel cysteine protease having a modified amino acid sequence of SEQ ID NO: 1, wherein glutamic acid at $180^{th}$ position (Glu180) (the number of the amino acid position is initiated from the mature domain (SEQ ID NO: 2) of VX-4) is deleted, or substituted with an amino acid selected from the group consisting of arginine, histidine, lysine, alanine, isoleucine, leucine, methionine, phenylalanine, proline, tryptophane, valine, cysteine, and the like. The cysteine protease is characterized in that its cysteine protease activity is maintained, but its substrate specificity is altered (for example, its substrate specificity against Z-RR-MCA at pH 7.5 is eliminated).

In addition, the present invention relates to a method of screening an anti-malarial agent against *Plasmodium vivax* comprising:

providing *Plasmodium vivax* cysteine protease (VX-4, AAT91956, SEQ ID NO: 1) or an expression vector comprising a polynucleotide encoding the VX-4;

contacting the VX-4 or the recombinant expression vector with a candidate material; and measuring at least one selected from the group consisting of:

(a) the degrading activity of the vivapain-4 or the expressed vivapain-4 from the recombinant expression vector against a dipeptidyl substrate favored by cathepsin L at pH 4.5 to 6.5, preferably approximately pH 5.5, wherein the dipeptidyl substrate has at least one hydrophobic amino acid;

(b) the degrading activity of the vivapain-4 or the expressed vivapain-4 from the recombinant expression vector against a dipeptidyl substrate favored by cathepsin B at pH 6.6 to 9, preferably pH 6.6 to 7.5, wherein the dipeptidyl substrate has at least one hydrophilic amino acid;

(c) the degrading activity of the VX-4 or the expressed VX-4 from the recombinant expression vector against actin at pH 6.8 to 7.2;

(d) the degrading activity of the VX-4 or the expressed VX-4 from the recombinant expression vector against hemoglobin at pH 5.5 to 6; and (e) the cleavage activity of the VX-4 against plasmepsin at pH 5-7.

The hydrophobic amino acid of (a) may selected from the group consisting of alanine, isoleucine, leucine, methionine, phenylalanine, proline, tryptophane, valine, cysteine, and the like. In the concrete embodiment of the present invention, benzyloxycarbonyl-L-phenylalanyl-L-arginine 4-methyl-coumaryl-7-amide (Z-Phe-Arg-MCA) or benzyloxycarbonyl-leucyl-L-arginine 4-methyl-coumaryl-7-amide (Z-Leu-Arg-MCA) is used as the dipeptidyl substrate of (a).

The hydrophilic amino acid of (b) is selected from aspartic acid, glutamic acid, arginine, histidine, and lysine. In the concrete embodiment of the present invention, benzyloxycarbonyl-L-arginyl-L-arginine 4-methyl-coumaryl-7-amide (Z-RR-MCA) is used as a dipeptidyl substrate of (b).

The activity of VX-4 may be measured by any conventional protein activity analysis means, for example, by fluorescence and the like, but not limited thereto.

Considering the importance of Glu180 in the activity of VX-4 as above, if the Glu180 is deleted, substituted with an amino acid having different property from glutamic acid, or inactivated, and the like, VX-4 loses its activities.

Therefore, another aspect of the present invention relates to a method of treating a parasitic disease caused by *Plasmodium vivax*, comprising:

administering a therapeutically effective amount of an inhibitor against *Plasmodium vivax* cysteine protease (VX-4, XP_001615272) to a patient in need of the treatment, wherein the inhibitor may be capable of inhibiting the expression of glutamic acid at 180$^{th}$ position (Glu180) in VX-4, substituting the Glu180 with an amino acid other than glutamate, or inactivating the Glu180. The method of treating a parasitic disease may include an additional step of identifying the patient in need of the parasitic disease treatment, before the step of administering the inhibitor. The parasitic disease refers to a disease caused by *Plasmodium vivax*, such as malaria.

Considering that glutamic acid is anionic (acidic) and hydrophilic, the inhibitor may one capable of substituting the Glu180 with a basic or hydrophobic amino acid, for example, selected from the group consisting of arginine, histidine, lysine, alanine, isoleucine, leucine, methionine, phenylalanine, proline, tryptophane, valine, cysteine, and the like.

Finally, VX-4 demonstrates pH-dependent substrate switching, which might offer an efficient mechanism for the specific cleavage of different substrates in different intracellular environments. VX-4 might be function as a hemoglobinase in the acidic parasite food vacuole, a maturase of *P. vivax* plasmepsin 4 at neutral or acidic pH, and a cytoskeleton-degrading protease in the neutral erythrocyte cytosol.

Although the foregoing invention has been described in detail by way of example for purposes of clarity of understanding, it will be apparent to the artisan that certain changes and modifications are comprehended by the disclosure and may be practiced without undue experimentation within the scope of the appended claims, which are presented by way of illustration not limitation. The following examples are provided to illustrate specific aspects of the invention and are not meant to be limitations.

A better understanding of the present invention may be obtained in light of the following examples that are set forth to illustrate, but are not to be construed to limit, the present invention.

BRIEF DESCRIPTION OF DRAWINGS

FIGS. 1A and 1B show a multiple alignment of amino acid sequence of vivapain-4 and its homologs in *Plamodium* genomes.

EXAMPLE

All animals used in this study were housed in accordance with guidelines from the Association for the Assessment and Accreditation of Laboratory Animal Care (AAALAC). All protocols were approved by the Institutional Review Board and conducted in the Laboratory Animal Research Center of Sungkyunkwan University.

Example 1

In Silico Identification of Cysteine Protease Gene 1.1: Sequencing of Novel Cysteine Proteases Genes putatively coding for cysteine proteases were identified from primate and rodent *Plasmodium* sequences deposited in PlasmoDB (http://plasmodb.org), TIGR (http://www.tigr.org), and GenBank (http://www.ncbi.nlm.nih.gov/) through BLAST searches. The amino acid (AA) sequences of cysteine proteases of *P. falciparum* (FP-2 [XP_001347836](SEQ ID NO: 19), FP-2B [XP_001347832](SEQ ID NO: 20), and FP-3 [XP_001347833](SEQ ID NO: 18)), *P. vivax* (VX-2 [XP_001615274] (SEQ ID NO: 14) and VX-3 [XP_001615273](SEQ ID NO: 16)), *P. yoelii* (yoelipain-2 [YP-2; XP_726900](SEQ ID NO: 21)), and *P. berghei* (bergheipain-2 [BP]-2 [XP_680416](SEQ ID NO: 22)), *P. chabaudi* (chabaupain-2 [CP-2], AAP43630(SEQ ID NO: 23)), *P. vinckei* (vinckepain-2 [VP-2], AAL48319(SEQ ID NO: 24)), *P. knowlesi* (knowlepain-2 [KP-2], CAQ39926 (SEQ ID NO: 15); KP-3, CAQ39925(SEQ ID NO: 17); and KP-4, CAQ39924(SEQ ID NO: 13)), *P. falciparum* (FP-2, XP_001347836(SEQ ID NO: 19); FP-2B, XP_001347832 (SEQ ID NO: 20); and FP-3, XP_001347833(SEQ ID NO: 18)), and *P. vivax* (VX-2 [XP_001615274] (SEQ ID NO: 14) and VX-3 [XP_001615273](SEQ ID NO: 16)) were used in multiple queries, with a threshold at 0.001 (E-value cut-off). After excluding redundancies, the AA sequences were aligned with ClustalX and optimized with GeneDoc. The alignment was used as an input in the construction of neighbor joining and maximum likelihood trees using PHYLIP (ver. 3.6b) and TREE_PUZZLE (ver. 5.2). The standard error in each of the connecting nodes was estimated by bootstrapping of 1000 replicates.

Two novel cysteine proteases isolated from *P. vivax* were annotated as *P. vivax* cysteine protease 1 (VX-1; XP_001615807) and 4 (VX-4; XP_001615272), according to their clustering patterns in the trees.

The obtained results revealed that the *P. vivax* genome encodes four closely related vivapains. By data-mining of the *P. vivax* genome (TIGR, Release 2.0), two genes putatively coding for novel cysteine proteases were identified, in addition to the previously identified genes encoding VX-2 (PlasmoDB code PVX_091415) and VX-3 (PVX_091410). The inventors designated these genes as VX-1 (PVX_195290) and VX-4 (PVX_091405). The other primate *Plasmodium* genomes examined, such as *P. falciparum*, *P. reichenowi* and *P. knowlesi*, also harbored four closely related cysteine protease genes. Conversely, avian and rodent malaria parasites including *P. gallinaceum*, *P. yoelii*, and *P. berghei* possessed only two paralogous genes (FIGS. 1A and 1B).

Figure 1A:
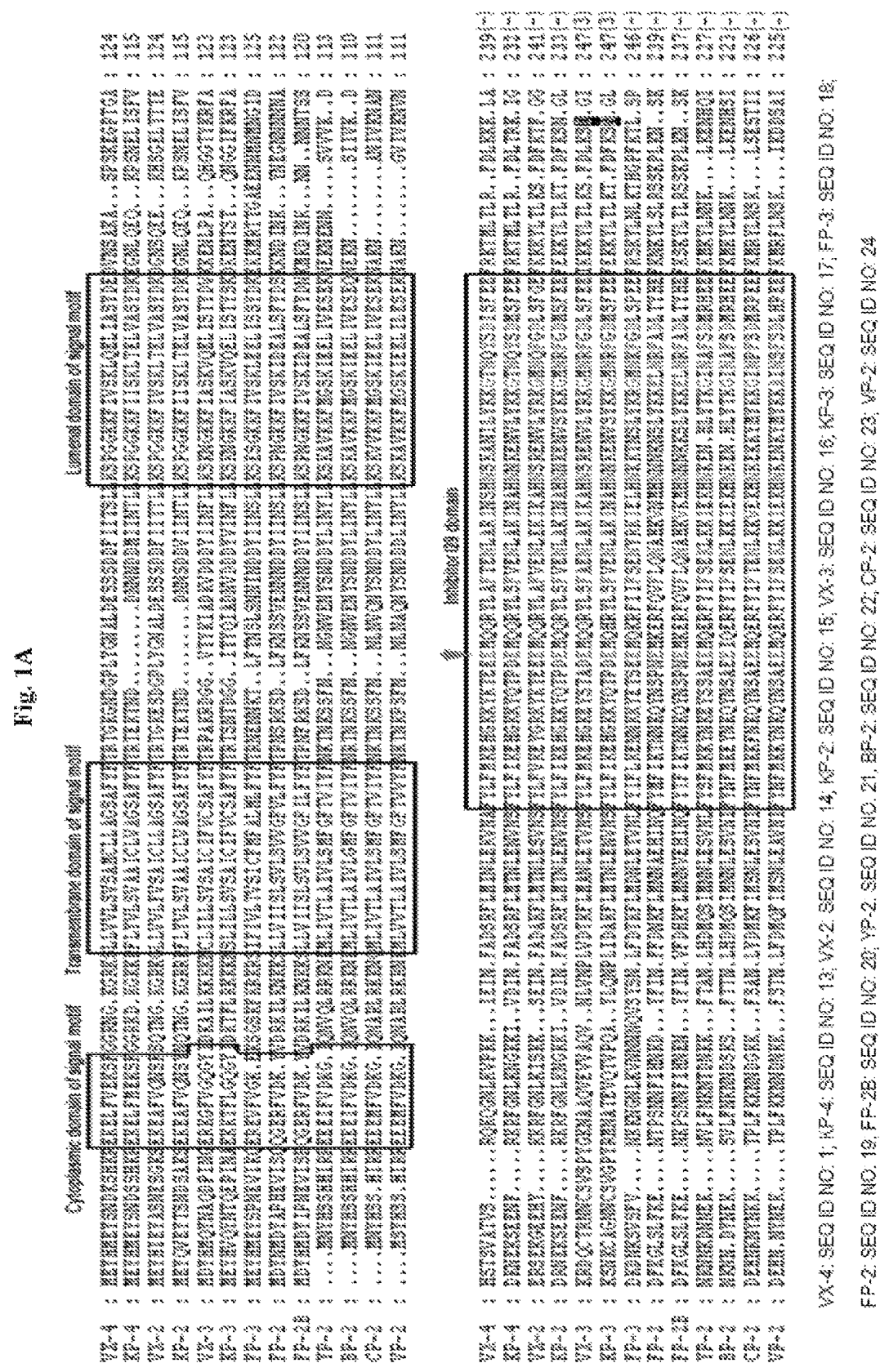
Figure 1B:
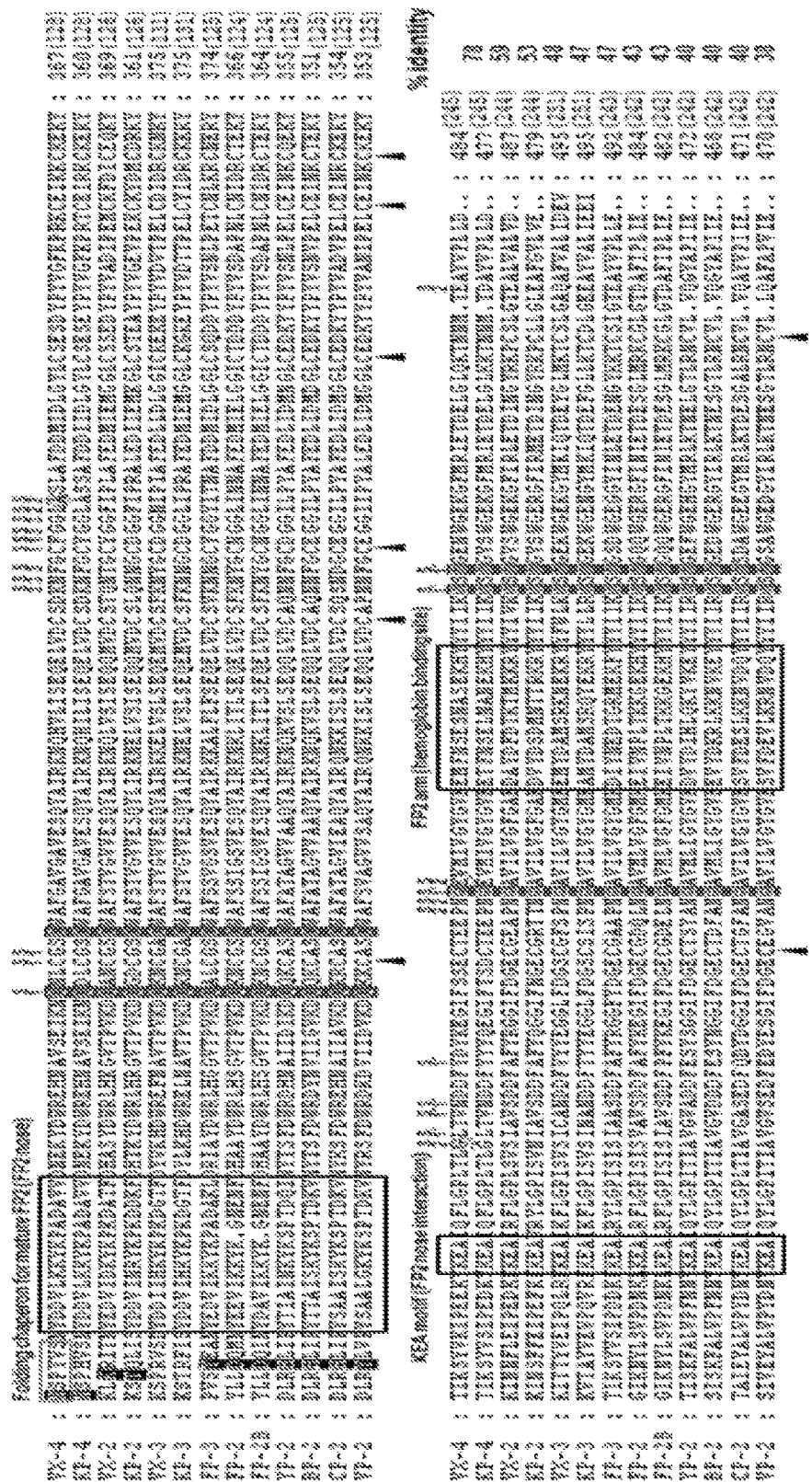

FIGS. 1A and 1B show a multiple alignment of amino acid sequence of vivapain-4 and its homologs in *Plamodium* genomes. Numbers of amino acids (AAs) in full-length polypeptides are marked at right side of each of the alignments and numerical in parentheses indicates those of mature forms. Dots indicate gaps introduced into the alignment to maximize similarity values. Boxes indicate sequence motifs of interest based on the FP-2 structure. The ERFNIN and GNFD signatures of prodomains are marked by red letters. Shading marks a putative starting position of each mature domain (SEQ ID NO: 2). Red arrow in inhibitor 129 domain box (FIG. 1A) indicates amino acid position corresponding to the N-terminal region of recombinant VX-4. Three AA residues of S2 pocket, which were selected for the mutagenesis experiments, are indicated by dotted red circles (FIG. 1B). In the figures, YP-2 refers to yoelipain-2 (XP_726900); BP-2, berghepain-2 (XP_680416); CP-2, chabaupain-2 (AAP43630); VP-2, vinckepain-2 (AAL48319); FP-2, falcipain-2 (XP_001347836); FP-2B, falcipain-2B (XP_001347832); FP-3, falcipain-3 (XP_001347833); KP-4, knowlepain-4 (CAQ39924); VP-4, vivapain-4 (XP_001615272); KP-2, knowlepain-2 (CAQ39926); VP-2, vivapain-2 (XP_001615274); KP-3, knowlepain-3 (CAQ39925); VP-3, vivapain-3 (XP_001615273).

The deduced AA sequence of VX-4 (TC5625, 484 AAs) revealed considerable degrees of identity to that of VX-2 (TC5622, 59%) and VX-3 (TC5618, 48%), while that of VX-1 (TC5613, 583 AAs) was highly related to the FP-1-like proteases of P. falciparum, P. knowlesi, P. ovale and P. fragile (37-77% identity). The greater length of VX-1 might be attributable to an N-terminal extension [Na B K, Kim T S, Rosenthal P J, Kong Y (2004) Evaluation of cysteine proteases of Plasmodium vivax as antimalarial drug targets: Sequence analysis and sensitivity to cysteine protease inhibitors. Parasitol Res 94:312-317].

Physiological implications and specific domain(s)/signature(s) of VX-1 remain largely elusive. The primary structure of VX-4 tightly conserved the AA residues lining the catalytic site (Gln, Cys, His, Asn and Trp) that are essential for the stabilization of a thiolate-imidazolium ion pair and/or the transition state of the catalytic site (AA positions highlighted in blue in FIG. 1B). As shown in FIGS. 1 and 1B, the regulatory motifs of the plasmodial cysteine proteases such as a bipartite trafficking domain, inhibitor domain with ERFNIN signature and hemoglobin-binding FP2 arm were also clearly identified in each of the corresponding regions.

The eight Cys residues, which are involved in the maintenance of structural geometry, were well conserved in these proteins, whereas the last Cys was replaced by Asn in VX-4 and KP-4 (arrowheads in FIG. 1B). Given the fact that a disulfide bridge between the seventh and eighth Cys residues is intimately engaged in the stabilization of the S2 and S1' sites of FP-2, the more flexible binding pocket of VX-4 might allow broader accessibility of proteolytic substrates. In addition, several AA substitutions found in critical domains of VX-4 suggest a distinctive physiological role for this protease (FIGS. 1A and 1B). These collective data demonstrate that VX-4 is a distinct cysteine protease that shares significant identity with, but clearly differs from previously characterized P. vivax cysteine proteases.

1.2: Phylogenetic Analysis

This experiment suggests that Plasmodium cysteine proteases exhibit differential evolutionary episodes along with their donor organisms.

Figure 2:
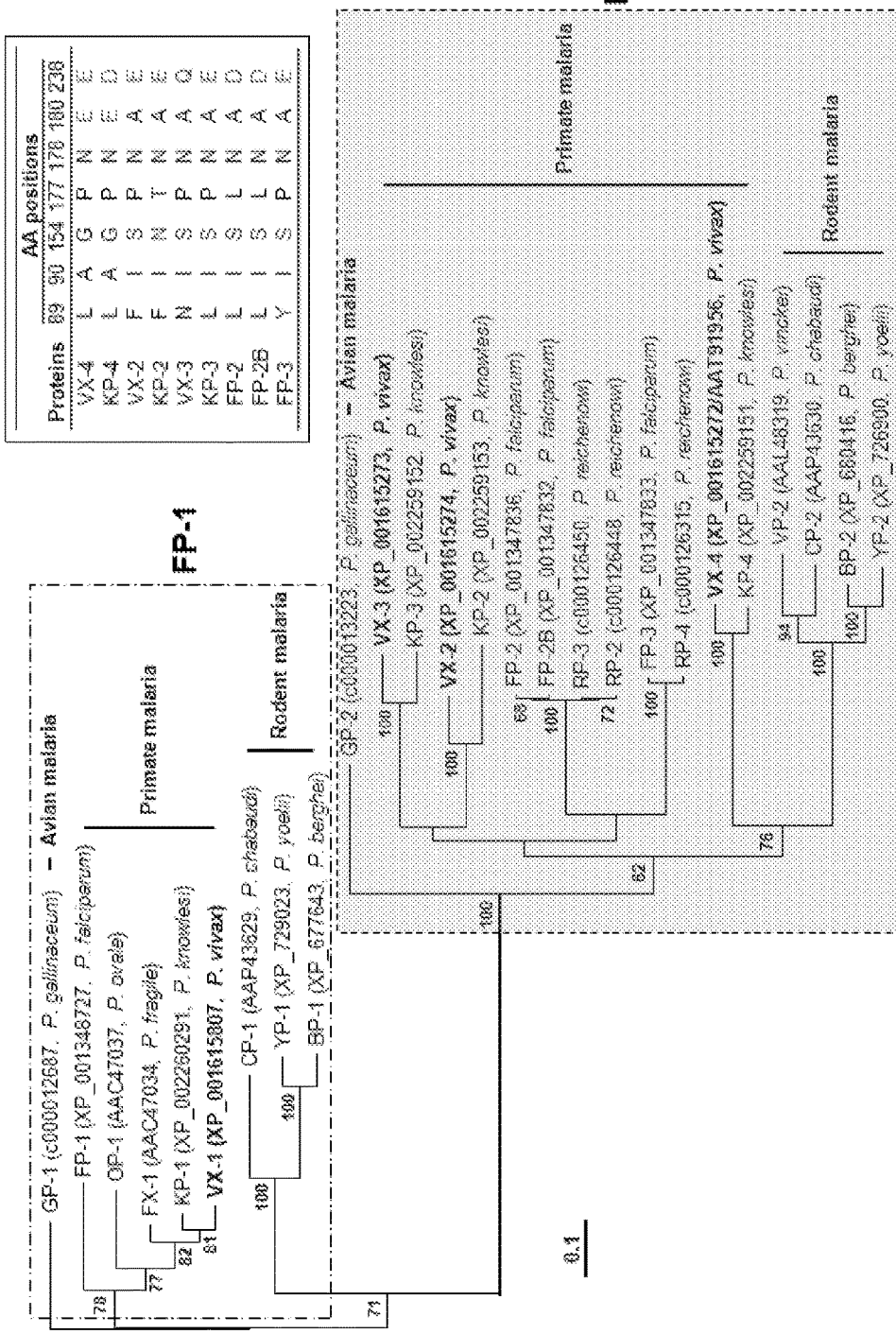
FIG. 2 shows results of phylogenetic analysis and amino acid substations of vavapain-4.

A neighbor-joining tree of VX-1 and VX-4 homologs, which were retrieved from PlasmoDB and GenBank, was constructed employing the AA sequences of mature domains (FIGS. 2). The Plasmodium proteases were largely separated into two distinct clusters consistent with their predicted biological roles: FP-1 clade, of which members are implicated in host cell invasion and oocyst production, and FP-2clade, the majority of which play central roles in hemoglobin degradation.

An overall topology similar to that of the neighbor-joining tree was observed in a quartet maximum likelihood tree (TREE_PUZZLE program; ver. 5.2) and the major branching nodes were supported by significant bootstrapping or quartet values. The falcipain homolog genes appeared to have duplicated from a common ancestor before diverging into each of the avian and mammalian parasite lineages. The FP-1-family proteins seemed to have diverged along with their specific donor organisms without any provocative genetic event. Meanwhile, members of FP-2 clade might have more complicated evolutionary pathways, including either multiplication(s) in primate malaria or deletion(s) in rodent malaria. The genes orthologous to VX-2 and VX-3 may have been deleted in the rodent parasites, considering the polytomic relationships among the P. vivax and P. knowlesi paralogs and the tight clustering of VX-4/KP-4 with rodent malarial proteins. This suggestion is further supported by the fact that P. falciparum and P. reichenowi, which comprise a basal clade in mammalian Plasmodium lineages, contain three paralogous genes. The three paralogous genes occupying distinct but highly linked genomic loci (cysteine protease island) may have undergone a kind of convergent evolution events in these basal malaria genomes.

FIG. 2 shows results of phylogenetic analysis of malaria cysteine proteases including VX-4. The phylogeny was based on the AA sequence alignment of mature regions. Divergence rates were calculated with the Jones-Taylor-Thornton (JTT) substitution model (see Jones D T, Taylor W R & Thornton J M (1992) The rapid generation of mutation data matrices from protein sequences. Computer Applications in the Biosciences 8: 275-282), and the tree was constructed using the neighbor joining algorithm (see Saitou N, Nei M (1987) The neighbor-joining method—a new method for reconstructing phylogenetic trees. Molecular and Biology and Evolution 4:406-425). The tree was rooted with GP-1 of Plasmodium gallinaceum, which was taken as an out-group. The number at each of the branching nodes indicates the likelihood (percentage) of its appearance in the bootstrapping analysis with 1000 replicates. The enzymes from P. vivax are in bold. The box indicates AAs found in the S2 pocket of primate plasmodial proteases, with position numbers based on mature VX-4. Red, blue, and black AAs are acidic, uncharged polar and hydrophobic, respectively. Note: The vivax protein with accession no. XP_001615272 was annotated as VX-2 during primary analysis of the whole genome sequence of the P. vivax Sal I strain. The name is changed to VX-4 according to our current result (AAT91956).

Adding to increased genic dosage, the degree of sequence divergence was prominent among the primate FP-2-clade members (0.812±0.078), compared to related rodent proteins (0.271±0.034). The members of primate (0.266±0.035) and rodent (0.377±0.056) FP-1 clade displayed values similar to that of the rodent FP-2-like proteins (Table 1).

TABLE 1

Pairwise divergence matrix of plasmodial falcipain homologs (FPs) based on the Jones-Taylor-Thornton model[a]

| Group[b] | 1 | 2 | 3 | 4 |
| --- | --- | --- | --- | --- |
| 1, Rodent FP-1 | 0.377 ± 0.056 | 1.261 ± 0.130 | 3.032 ± 0.480 | 2.735 ± 0.393 |
| 2. Primate FP-1 | | 0.266 ± 0.035 | 2.840 ± 0.366 | 2.466 ± 0.338 |

TABLE 1-continued

Pairwise divergence matrix of plasmodial falcipain homologs (FPs) based on the Jones-Taylor-Thornton model[a]

| Group[b] | 1 | 2 | 3 | 4 |
|---|---|---|---|---|
| 3. Rodent FP-2 | | | 0.271 ± 0.034 | 0.917 ± 0.0112 |
| 4. Primate FP-2[c] | | | | 0.812 ± 0.078 |

[a]Distance values are presented as mean ± standard error. The standard error was computed by bootstrapping of 1,000 replicates after removing gaps as missing information in a pairwise manner.
[b]The malaria cysteine proteases were categorized into each of the groups based on a phylogenetic analysis (see FIG. 2).
[c]The highly redundant cysteine proteases of *P. falciparum* (FP-2B) and *P. reichenowi* (RP-3) were excluded in the analysis.

Alteration in gene copy number provides a simple way to change expression levels or to enlarge protein pools with non-overlapping functions. Biochemical studies have demonstrated that the primate malaria proteins belonging to the FP-2 clade exhibit similar enzymatic properties; however, those of *P. vinckei* (VP-2) and *P. berghei* (BP-2) demonstrated quite dissimilar features, particularly in terms of their substrate preference and inhibitor specificity. Therefore, the large divergence among the primate FP-2 proteins and tight clustering of VX-4 and KP-4 with rodent *Plasmodium* proteins (bootstrapping value 76) further suggest biological roles of VX-4 that are distinct from those previously described for VX-2 and VX-3.

Example 2

Expression and Refolding of a Recombinant VX-4 (rVX-4)

The open reading frame (ORF) of VX-4 was amplified with forward (5'-ATGGAATATCACATGGAGTACTC-GAAC-3', SEQ ID NO: 3) and reverse (5'-CTAGT-CAAGCAGGGGGACGTACGCCTC-3', SEQ ID NO: 4) primers using Ex Taq DNA polymerase (Takara, Japan) and *P. vivax* genomic DNA (100 ng) isolated from a Korean patient (a generous gift from Dr. J S Yeom [Sungkyunkwan University Hospital]). The PCR conditions were as follows:

94° C. 5 min
94° C. 1 min, 50° C. 1 min, 72° C. 2 min: 30 cycles
72° C. 10 min

The product was gel-purified, ligated into the pCR2.1 vector (Invitrogen, CA) nd transformed into competent *E. coli* Top10 cells (Invitrogen) by heat shock (ice 30 minutes, 42° C. 45 seconds, ice 5 minutes). The purification, ligation and transformation were conducted according to a manual provided by Invitrogen. The nucleotide sequence was determined with an ABI PRISM 377 DNA sequencer (Applied Biosystems, CA).

The obtained DNA fragment harboring the mature region and a portion of the prodomain from AA position 182 of SEQ ID NO: 1 were amplified using Ex Taq DNA polymerase (Takara, Japan) and 2 primers; 5'-GAGCTCGAGAT-GCAGCAGAGGTACCT-3' (SEQ ID NO: 5, containing a 5' Sac I site) and 5'-CTGCAGCTAATCCACGAGCG-CAACGA-3' (SEQ ID NO: 6, containing a 5' Pst I site).

The PCR conditions were as follows:

94° C. 5 min
94° C. 1 min, 50° C. 1 min, 72° C. 2 min: 30 cycles
72° C. 10 min

The PCR product was ligated and transformed as described above, and ligated into the pQE-30 expression vector (Qiagen, CA) using Sad and PstI. The plasmid was transformed into competent *E. coli* M15 (pREP4) cells (Qiagen) by heat shock (ice 30 minutes, 42° C. 45 seconds, ice 5 minutes), grown overnight in LB broth (containing 100 ug/ml ampicillin and 50 ug/ml kanamycine) and induced with 1 mM isopropyl-1-thio-β-D-galactopyranoside for 3 h at 37° C. The bacterial cells were suspended in lysis buffer (8 M urea, 10 mM Tris-HCl, 100 mM NaH2PO4, pH 8.0) and then centrifuged at 12,000 g for 20 minutes to collect supernatant.

rVX-4 was purified from the supernatant by nickel-nitrilotriacetic acid (Ni-NTA agarose, Qiagen) chromatography, following the manufacturer's instruction. Optimal refolding conditions for rVX-4 were determined with 100 different buffer combinations in a microplate format [Sijwali P S, Brinen L S, Rosenthal P J (2001) Systematic optimization of expression and refolding of the *Plasmodium falciparum* cysteine protease falcipain-2. Protein Expr Purif 22:128-134].

The expressed and purified rVX-4 protein comprising a portion of the prodomain and entire mature domain was subject to 12% SDS-PAGE analysis with coomassie blue staining, and the obtained results are shown in FIG. 3(A) (Lanes a, uninduced *E. coli* lysate; b, IPTG-induced *E. coli* lysate; c, Ni-NTA purified rVX-4. $M_r$, molecular masses in kDa).

For large-scale refolding, purified rVX-4 (100 mg) was diluted 100-fold in optimized refolding buffer (250 mM L-arginine, 1 mM ethylenediaminetetraacetic acid [EDTA], 5 mM reduced glutathione [GSH], 1 mM oxidized glutathione [GSSG], and 100 mM Tris-HCl, pH 8.0), and incubated overnight at 4° C. To allow processing to the active enzyme, the pH was adjusted to 5.5 in the presence of 10 mM dithiothreitol (DTT), the sample was incubated at 37° C. for 2 h, and the pH was then readjusted to 6.5. The protein was concentrated with a Centriprep concentrator (cut-off: 10 kDa, Millipore).

The rVX-4, which was refolded followed by maturation under reducing and mild acidic (pH 5.5) conditions, was subject to 12% SDS-PAGE analysis with coomassie blue staining, and the obtained results are shown in FIG. 3(B). FIG. 3(B) shows processing of the refolded rVX-4. The purified rVX-4 was refolded and activated, and aliquots collected every 30 min were analyzed by 12% SDS-PAGE with Coomassie staining (left). The proteolytic activity of fully processed rVX-4 was analyzed by a gelatin gel-zymogram (right). The fully processed 28 kDa protein (left panel, FIG. 2(B)) exhibited protease activity by gelatin-gel electrophoresis (right panel, FIG. 2(B)), which was completely inhibited by the cysteine protease inhibitor E-64.

Example 3

N-Terminal Amino Acid Sequencing

The fully processed rVX-4 was separated by 12% SDS-PAGE. The protein was transferred to a polyvinylidene difluoride (PVDF) membrane (Millipore) and stained with Coomassie blue. The band was excised and subjected to protein sequencing on an ABI model 477A protein sequencer and an ABI model 120A PTH analyzer (Applied Biosystems) at the Korea Basic Science Institute (Daejeon, Korea). The obtained N-terminal amino acid sequence is shown in red box of FIG. 1B, from which mature rVX-4 is initiated.

Example 4

Specific Antibodies

Six-week-old, specific pathogen free (SPF) BALB/c female mice were subcutaneously immunized 3 times with the purified rVX-4 (30 μg per each mouse per each time) in Freund's adjuvants (Sigma-Aldrich) at 2-week intervals. One week after the final inoculation, 10 μg protein were injected via tail vein. One week later, the blood was collected by heart puncture, after which the antiserum was prepared. BALB/c mouse (6-week-old) serum obtained from SPF strain was used as a normal control.

Example 5

Cysteine Protease Activity Assay and Kinetics

Cysteine protease activity was ascertained by the hydrolysis of benzyloxycarbonyl-L-leucyl-L-arginine 4-methyl-coumaryl-7-amide (Z-LR-MCA) (Peptide International, Louisville, Ky.). Enzyme (xVX, 30 μl; 200 nM) was added to 100 mM sodium acetate (220 μl, pH 5.5) containing 5 μM Z-LR-MCA and 10 mM DTT. The release of fluorescence was assessed at excitation and emission wavelengths of 355 nm and 460 nm with a SpectraMAX Gemini fluorometer (Molecular Devices, Sunnyvale, Calif.).

For activity gel electrophoresis, the obtained refolded rVX-4 was mixed with SDS-PAGE sample buffer lacking 2-mercaptoethanol and subjected to 12% SDS-PAGE co-polymerized with 0.1% gelatin. The gel was washed with 2% Triton X-100 (30 min), incubated overnight with 100 mM sodium acetate (pH 5.5) containing 10 mM DTT at 37° C. and stained with Coomassie Blue.

For kinetic analysis, the rVX-4 (25 nM) was incubated with varying concentrations of peptide substrates (Z-LR-MCA) at pH 5.5, 6.5 and 7.5 in appropriate buffers (100 mM sodium acetate (pH 4.5-5.5), 100 mM sodium phosphate (pH 6.0-6.5) and 100 mM Tris-HCl (pH 7.0-8.5)), each supplemented with 10 mM DTT. The release of MCA was monitored over 10 min at room temperature as described above. Activities were compared as fluorescence over time. The kinetic constants $K_m$ and $V_{max}$ were determined using GraphPad software.

The optimal pH was assessed in 100 mM sodium acetate (pH 4.5-5.5), 100 mM sodium phosphate (pH 6.0-6.5) and 100 mM Tris-HCl (pH 7.0-8.5). The enzymes (50 nM) were added to each buffer supplemented with 10 mM DTT and 5 μM Z-L-phenylalanyl-L-arginine 4-methyl-coumaryl-7-amide (Z-FR-MCA), Z-leucyl-L-arginine-MCA (Z-LR-MCA), or Z-L-arginyl-L-arginine 4-methyl-coumaryl-7-amide (Z-RR-MCA) (Peptide International). The appropriate buffers were separately employed as controls at each pH. Enzyme activity was measured as described above. The effects of reducing agents were examined under various concentrations of GSH, and pH stability was examined at pH 5.0 and 8.0 by incubating rVX-4 at 37° C. in the appropriate buffer. Active site titration was done using a specific inhibitor, trans-epoxysuccinyl-L-leuciloamido-(4-guanidino) butane (E-64).

rVX-4 hydrolyzed synthetic dipeptidyl substrates with hydrophobic AA residues at their P2 site such as Z-LR-MCA and Z-FR-MCA under acidic conditions as described above. The determined enzyme activity, stability, and inhibition of The VX-4 are shown in FIGS. 3(C), 3(D), and 3(E), respectively.

Figure 3:
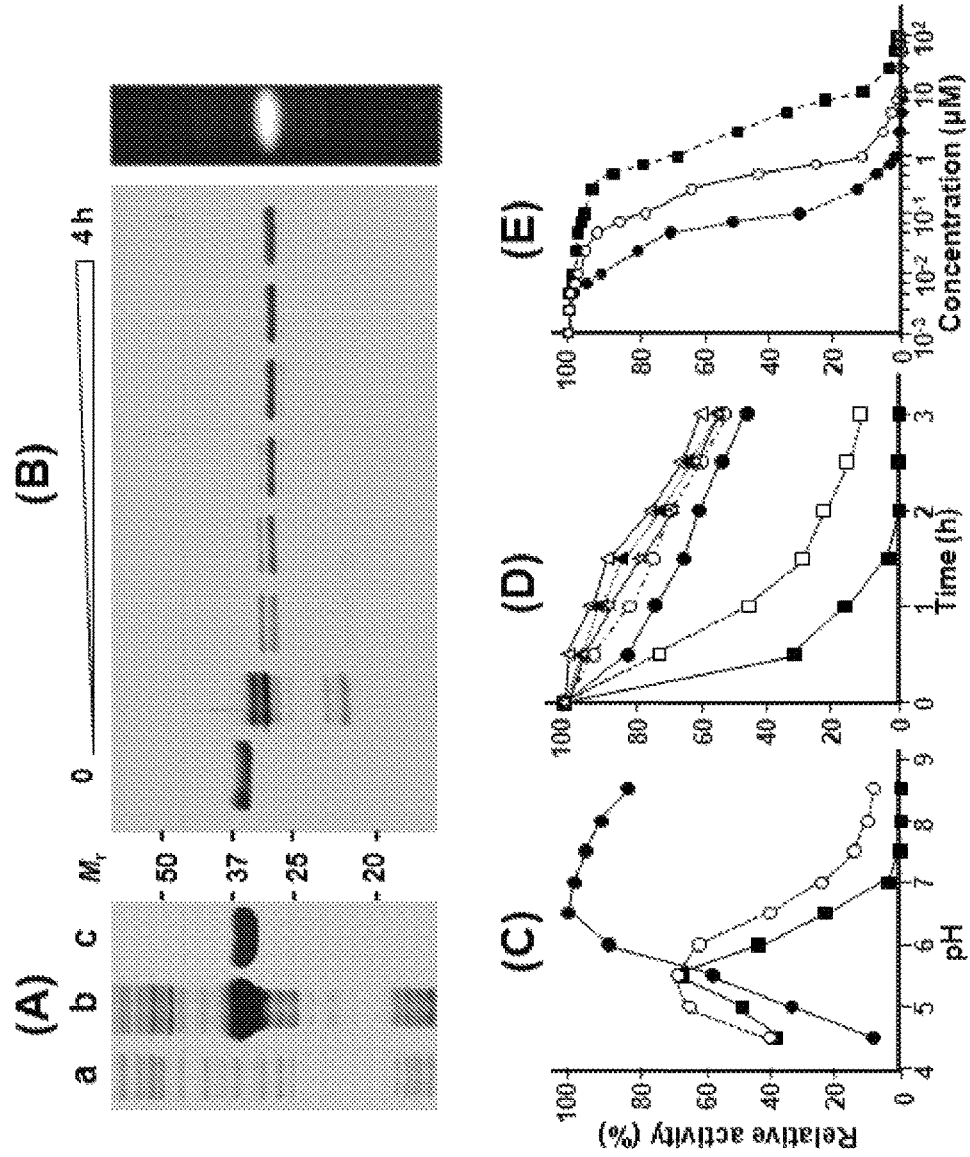
FIG. 3 shows biochemical properties of recombinant vivapain-4.

FIG. 3(C) relates to determination of pH optimum. The VX-4 enzyme activity was assayed in 100 mM sodium acetate (pH 4.5-5.5), sodium phosphate (pH 6.0-6.5) or Tris/HCl (pH 7.0-8.5), each supplemented with 10 mM DTT. Activity was measured at 37° C. each against Z-FR-MCA (■), Z-LR-MCA (○), and Z-RR-MCA (●). Maximal activity was presented as 100%. As shown in FIG. 3(C), the enzymatic activity was highest at pH 5.5. The pH-optimum was substantially different with a substrate containing a basic AA at P2 (Z-RR-MCA) with maximal activity at pH 6.5, and activity seen above pH 8. These results suggest either that electrostatic conditions near the S2 site are highly dependent on the surrounding pH or that the geometry of the catalytic site can be changed in a pH-dependent manner.

FIG. 3(D) relates to determination of enzyme stability depending on pH. rVX-4 was incubated at different pHs in the respective buffers as in panel C. Residual activity was assayed with Z-LR-MCA in 100 mM sodium acetate (pH 5.5) supplemented with 1 mM DTT after indicated incubations at pH 4.5 (●), 5.0 (○), 5.5 (▲), 6.0 (Δ), 7.0 (☆), 8.0 (□) and 8.5 (■). rVX-4 was relatively stable after incubation at acidic and neutral pH, while it was highly unstable under alkaline conditions (pH 8.0 and 8.5) against Z-LR-MCA, which was similar to results observed for FP-2 and FP-3. These data suggest that decreased hydrolyzing activity of rVX-4 against Z-LR-MCA and Z-FR-MCA at alkaline conditions might be due to an irreversible change of the protein conformation.

FIG. 3(E) shows a inhibition profile for E-64, which was determined by incubating rVX-4 (1 μM) with different concentrations of E-64 in 100 mM sodium acetate (pH 5.5; ●), 100 mM sodium phosphate (pH 6.5; ○) or 100 mM Tris-HCl (pH 7.5; ■) at room temperature for 30 min. Residual activities (%) were determined using Z-LR-MCA as a substrate. The requirement for increased concentrations of E-64 to inhibit rVX-4 at higher pH also supports altered structural geometry as the explanation for altered substrate preference.

Steady-state kinetic analyses confirmed varied substrate utilization depending on pH, and the obtained results are shown in Table 1.

TABLE 1

Comparison of substrate hydrolysis kinetics for vivapains

| | | $k_{cat}/K_m$ ($s^{-1}M^{-1}$) | | |
|---|---|---|---|---|
| | | VX-2 | VX-3 | VX-4 |
| pH 5.5 | Z-FR-MCA | NH[a] | NH | $1.55 \times 10^4$ |
| | Z-LR-MCA | $7.05 \times 10^5$ | $8.62 \times 10^4$ | $1.65 \times 10^4$ |
| | Z-RR-MCA | NH | NH | $1.34 \times 10^4$ |
| pH 6.5 | Z-FR-MCA | NH | NH | $5.52 \times 10^3$ |
| | Z-LR-MCA | $7.34 \times 10^5$ | $6.36 \times 10^4$ | $8.84 \times 10^3$ |
| | Z-RR-MCA | NH | NH | $3.49 \times 10^4$ |

TABLE 1-continued

Comparison of substrate hydrolysis kinetics for vivapains

| | | $k_{cat}/K_m$ (s$^{-1}$M$^{-1}$) | | |
|---|---|---|---|---|
| | | VX-2 | VX-3 | VX-4 |
| pH 7.5 | Z-FR-MCA | NH | NH | NH |
| | Z-LR-MCA | $4.15 \times 10^5$ | $6.26 \times 10^3$ | $3.05 \times 10^3$ |
| | Z-RR-MCA | NH | NH | $3.45 \times 10^4$ |

Activity values for each enzyme represent mean from three independent experiments.
$^a$NH, no hydrolysis.

As shown in Table 1, rVX-4 showed a similar catalytic efficiency against three peptide substrates at pH 5.5. However, at pH 7.5 $k_{cat}/K_m$ against Z-RR-MCA increased 2.6-fold whereas that against Z-LR-MCA decreased 5.6-fold and Z-FR-MCA was not hydrolyzed. The rVX-2 and rVX-3 proteins exhibited much higher $k_{cat}/K_m$ values than that of rVX-4 toward Z-LR-MCA at the pH conditions selected, although the optimal pH for rVX-2 was 6.5, rather than 5.5. Interestingly, rVX-2 and rVX-3 could not hydrolyze Z-FR-MCA or Z-RR-MCA. Phe has a large aromatic R group, and it might not fit into the S2 pocket of rVX-2 and rVX-3, which are stabilized by the disulfide bond between the seventh and eighth Cys residues (FIGS. 1A and 1B).

Example 7

Hydrolysis of Macromolecular Substrates

To observe possible roles of VX-4 in the processing of plasmepsin (PM), the inventors cloned *P. vivax* plasmepsin (PvPM) 4 (XM_001616821) and 5 (XM_001615583) employing *P. vivax* genomic DNA obtained from the Korean patient as previously described [Dame J B, Yowell C A, Omara-Opyene L, Carlton J M, Cooper R A, Li T (2003) Plasmepsin 4, the food vacuole aspartic proteinase found in all *Plasmodium* spp. infecting man. Mol Biochem Parasitol 130:1-12].

Recombinant PvPMs expressed in *E. coli* cells were purified by Ni-NTA chromatography (Qiagen) and refolded as described above. rVX-4 (50 nM) was incubated with PvPMs (20 μg each) in 100 mM sodium acetate (pH 5.0-5.5), 100 mM sodium phosphate (pH 6.0-6.5), or 100 mM Tris-HCl (pH 7.0-7.5) supplemented with 10 mM DTT for 3 h. The experiments were also performed in the presence of E-64 (1 μM) and/or pepstatin A (10 μM, Sigma-Aldrich). Hemoglobinase activity of rVX-4 (30 nM), as well as those of rVX-2 and rVX-3 expressed as previously described [Na B K, Shenai B R, Sijwali P S, Choe Y, Pandey K C, Singh A, Craik C S, Rosenthal P J (2004) Identification and biochemical characterization of vivapains, cysteine proteases of the malaria parasite *Plasmodium vivax*. Biochem J 378:529-538], was assessed using human hemoglobin (Sigma-Aldrich) in different pHs (5.0-7.5) in the presence of 1 mM GSH at 37° C.

Erythrocyte ghosts purified from fresh human blood by hypotonic lysis were incubated with rVX-4 (200 nM) at pH 7.0 or 7.5 at 37° C. for 3 h, after which reaction products were analyzed by reducing SDS-PAGE. For immunoblotting, the electrophoretically resolved proteins (rVX-4) were transferred to PVDF membranes (Millipore) followed by blocking with 0.05% Tween 20 in phosphate buffered saline (PBST) containing 2% bovine serum albumin. The membrane was incubated with appropriate antibodies including anti-human spectrin (Sigma-Aldrich, 1:500 dilutions), anti-human band 3 (Sigma-Aldrich, 1:3000 dilutions), or anti-human actin (Sigma-Aldrich, 1:1000 dilutions). Blots were subsequently incubated with horseradish peroxidase-conjugated host specific antibodies (Cappell). The immunoreactive bands were visualized using 4-chloro-1-naphthol (4C1N; Sigma-Aldrich) supplemented with 3% hydrogen peroxide.

The obtained results suggest that VX-4 may exert its activity in maturation of plasmepsin and digestion of erythrocytic actin, while having adjuvant roles in hemoglobin hydrolysis. Comparative analysis revealed that two motifs, the FP2 nose and FP2 arm, specific to the hemoglobin-degrading falcipain homologs, were conserved in VX-4 (FIGS. 1A and 1B). The FP2 nose interacts with the protease core via a highly conserved KEA motif to provide proper folding of the mature protein, while the FP2 arm mediates interaction between the enzyme and hemoglobin. The inventors recognized some differences in the FP2 arm motif of VX-4, in which residues Phe192, Ser194 and Ala198 (numbered from the mature sequence of VX-4) showed different degrees of hydropathy compared to those of other VXs. In addition, Ala198 of VX-4 offered a unique hydrophobic polymorphism, which in structural modeling contributed considerable change in the arm structure. These observations suggested that VX-4 may act principally on substrates other than hemoglobin.

It was assessed whether VX-4 plays a role in plasmepsin processing since a recent study has revealed that FPs function as maturases for plasmepsins within the food vacuole of *P. falciparum*. *Plasmodium* species infecting mammals harbored genes for seven PMs (PM4-PM10), of which PM4 orthologs were found in the food vacuole. *P. falciparum* genome encoded additional food vacuole-related proteins, PM1, PM2, and histo-aspartic protease (HAP), although genes orthologous to these proteins genes were not detected in non-falciparum species. These results suggest that PvPM4 is the major, if not all, plasmepsin targeted into the food vacuole of *P. vivax*.

Figure 5:
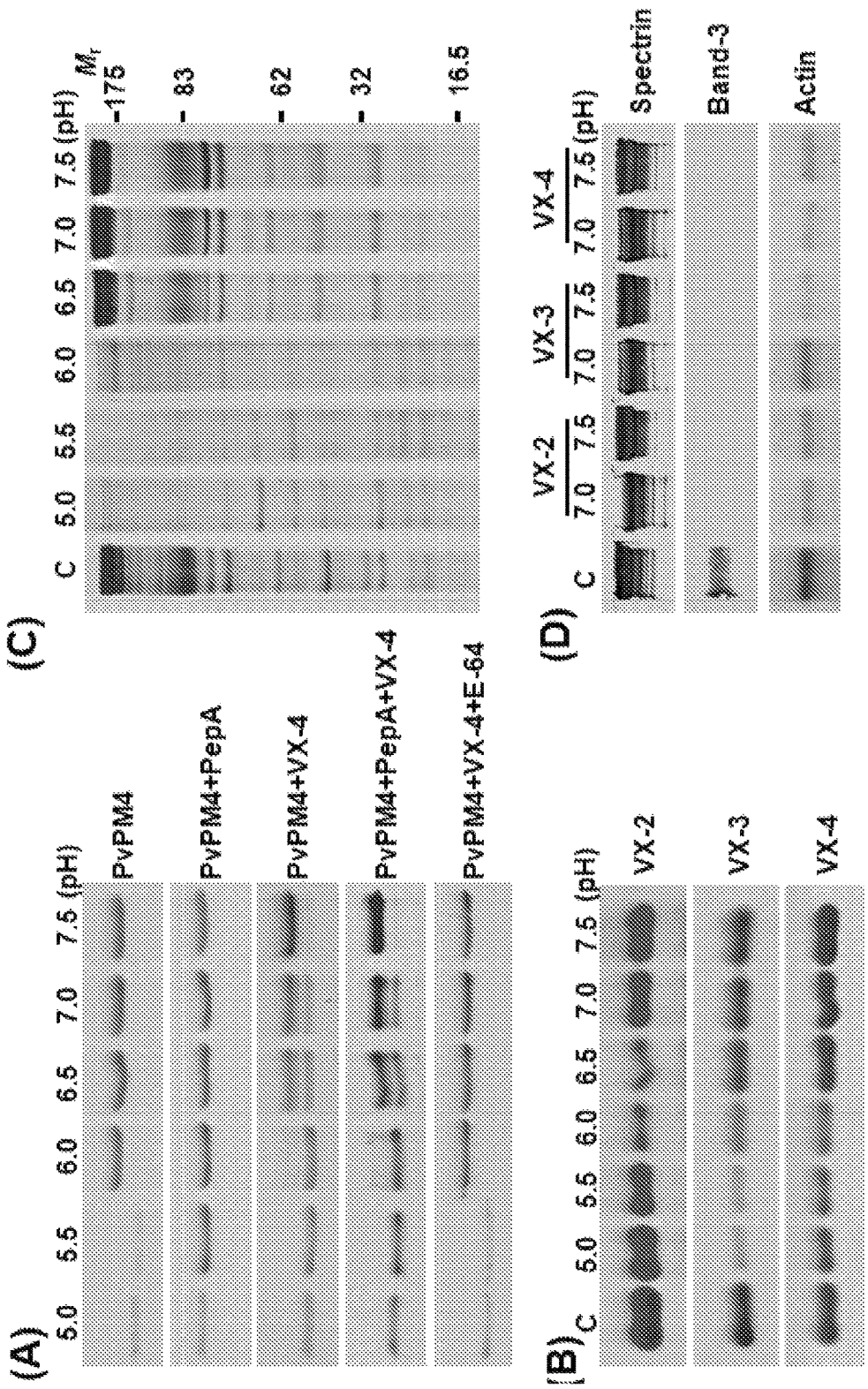
FIG. 5 shows reactivity of vivapain-4 against macromolecular substrates.
Figure 6:
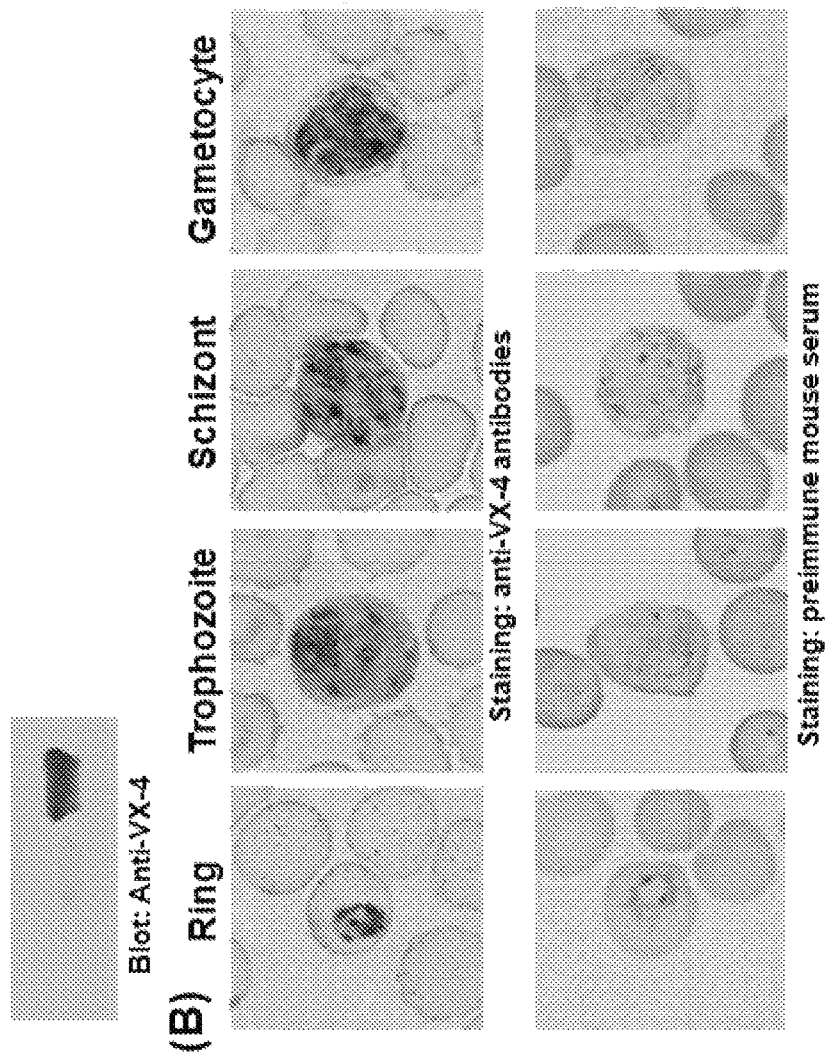
FIG. 6 shows spatiotemporal localization of vivapain-4 by immunocytochemical staining.

The inventors examined possible roles for VX-4 during maturation of recombinant PvPM4 (rPvPM4), which was expressed in *E. coli* as above, and the results are shown in FIG. 5(A). FIG. 5(A) relates to processing of *P. vivax* plasmepsin 4 (PvPM4) by rVX-4. Recombinant PvPM 4 (20 μg) was incubated with rVX-4 (50 nM) supplemented with 10 mM DTT at different pH values with or without pepstatin A (PepA, 10 μM) or E-64 (1 μM) for 3 h at 37° C. The reactants were analyzed by 12% SDS-PAGE. As shown in FIG. 5(A), autocatalytic processing of rPvPM4 occurred at acidic pH and, to a less extent, at neutral pH (6.5-7.0). This processing was completely blocked by the aspartic protease inhibitor pepstatin A. This cleavage was significantly accelerated in the presence of VX-4 in a dose- and time-dependent manner. In the presence of pepstatin A to block autocatalysis, rVX-4 effectively cleaved rPvPM4 at pH 5.0-7.0, and this process was specifically and significantly inhibited by E-64. These results suggest that VX-4 is a key molecule regulating PvPM4 maturation. Processing may occur during trafficking of the enzymes from endoplasmic reticulum (ER)-derived transport vesicles or the parasitophorous vacuolar space (PVS), where pH is neutral, or in the acidic food vacuole (pH 5.4-5.5). VX-2/VX-3 might also participate in the processing in the food vacuole.

The major hemoglobinases of *P. falciparum* are targeted into the food vacuole through ER-derived vesicles, but it is unclear whether the ER-derived, protease-containing vesicles fuse with hemoglobin-containing transport vesicles derived from cytosomes, or if they directly contact the food vacuole. The bipartite signals, composed of cytoplasmic, transmembrane and lumenal motifs, were found to be required for trafficking of FP-2 and FP-3 to the food vacuole, and they are conserved in VX-2, VX-3, and VX-4 (FIGS. 1A and 1B). The hemoglobinase activity of VX-4 was compared to that of VX-2 and VX-3. pH-dependent and time-lapse analyses demonstrated that the hemoglobinolytic activity of VX-4 was relatively weak. Maximal hemoglobin degrading activity of VX-2, VX-3 and VX-4 was observed between pH 6.0-6.5, 5.0-6.0, and 5.5-6.0, respectively (FIG. 5(B)). FIG. 5(B) shows the comparison of hemoglobinolytic activity of VX-2, VX-3 and VX-4. Native human hemoglobin was incubated with the respective enzymes in appropriate buffers (pH ranges 5.0-7.5) supplemented with 1 mM GSH for 3 h at 37° C., after which resolved by 10% SDS-PAGE. Considering their peak activities at different pHs, the action points of different VXs may be temporally segregated during hemoglobin degradation. However, it is unclear whether the biochemical differences between VX-2, VX-3, and VX-4 are most important to foster cooperative action against hemoglobin or to provide activities against different substrates over the course of erythrocytic infection by *P. vivax*.

To consider other potential substrates for VX-4, hydrolytic activity against erythrocyte cytoskeletal proteins was examined, and the results are shown in FIGS. 5(C) and 5(D). FIG. 5(C) shows the results of hydrolysis of erythrocyte membrane proteins by rVX-4 at different pHs. Fresh erythrocyte ghosts were incubated with rVX-4 in appropriate buffers (pHs 5.0-7.5) for 3 h at 37° C. and reaction products were analyzed by 10% SDS-PAGE. Molecular masses in kDa are shown to the right. FIG. 5(D) shows the results of western blotting of erythrocyte ghost proteins. The reactions were done at pH 7 and 7.5. The reactants were separated by 10% SDS-PAGE, transferred to a PVDF membrane and probed with specific antibodies against human erythrocyte spectrin (1:500), band 3 (1:30000) and actin (1:1000) followed by horseradish peroxidase conjugated anti-human IgG (1:1000). The blots were developed with 4C1N. C, control without enzyme.

VX-4 cleaved the majority of erythrocytic ghost proteins under acidic conditions (pH 5.0-6.0), whereas some activities were negligible at neutral pH (6.5-7.5). However, VX-2, VX-3, and VX-4 all degraded band-3 (anion exchanger 1, AE1) and actin at neutral pH. The proteolytic activities of VX-4 against erythrocyte actin and band-3 suggest an additional role for the protease in remodeling of erythrocyte cytoskeleton during the process of egress of merozoites from erythrocytes at the conclusion of the parasite erythrocytic cycle. Alternatively, actin degradation may be directly related to hemoglobin transport into the food vacuole, as a recent study showed that actin filament turnover in *P. falciparum* might be essential for both cytostome formation and hemoglobin translocation.

Example 8

Comparative Protein Structure Modeling

Computational analyses were accomplished in a Silicon Graphics Octane 2 workstation, equipped with two parallel R12000 processors (SGI). Homology modeling was orchestrated within the SYBYL 6.9 COMPOSER module (Tripos Associates, MO). Energy minimization and molecular dynamic studies were performed with the DISCOVER module of InsightII 2000 (Accelrys). The geometrical and local environmental consistency of the model was assessed within the PROSTAT and InsightII 2000 Profiles-3D modules, together with the SYBYL 6.9 Matchmaker module. Structural models of FP-2, FP-3, VX-2, VX-3 and VX-4 mature domains were prepared on the basis of their sequence homology with several cysteine proteases using an analogous approach [Desai P V, Avery M A (2004) Structural characterization of vivapain-2 and vivapain-3, cysteine proteases from *Plasmodium vivax*: comparative protein modeling and docking studies. J Biomol Struct Dyn 21:781-790]. More than 35% sequence identity was observed between the protein homologs and the target AA sequence. The homologs used in this analysis included human cathepsins K (1ATK), V (1FH0) and S (1MS6); cruzain (1AIM), a cysteine protease from *Ginger rhizome* (1CQD) and actinidin (1AEC). Terms in parentheses refer to the Protein DataBank accession numbers for the corresponding crystal structures.

Figure 4:
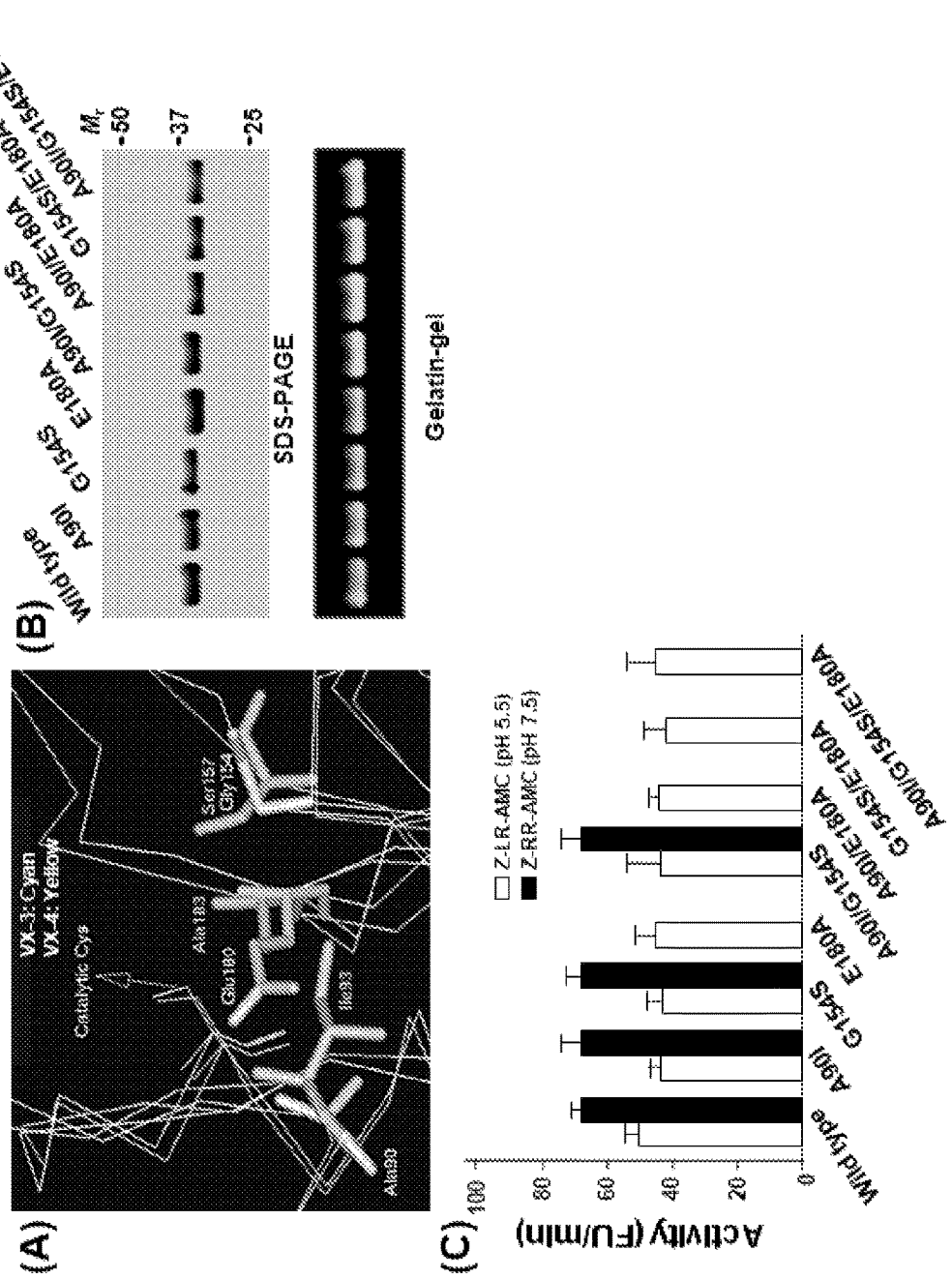
FIG. 4 shows results of modeling and mutation analyses.

Homology modeling of VX-4 demonstrated an overall topology similar to those of FP-2, FP-3, VX-2 and VX-3 with the average pairwise RMSD of 0.98 for the Cα atoms as above. However, a number of substitutions are recognized between VX-4 and the other VXs, including three prominent AA residues delineating the S2 pocket (Ala90, Gly154 and Glu180; numbering from the mature domain (SEQ ID NO: 2) of VX-4) (FIG. 4(A); see also box in FIGS. 1A, 1B, and 2). FIG. 4(A) shows superimposition of amino acid residues lining the binding pockets in VX-3 (cyan) and VX-4 (yellow). The residues are shown as sticks and the numbers of residues are indicated in reference to the corresponding enzymes.

Example 9

Mutation Analyses

Site-directed mutagenesis was performed using a Quick-Change II Site-Directed Mutagenesis Kit (Stratagene, Calif.). A pair of complementary primers with 39 bases was designed and a mutation to replace Ala90 to Ile (A90I), Gly154 to Ser (G154S) or Glu180 to Ala (E180A) was placed in the middle of the primers, as follows:

```
Primers for mutation of Ala90 to Ile (A90I)
Forward:
                                         (SEQ ID NO: 7)
5'-GGCTGCTTTGGTGGTTTAATCTCCCTTGCATTCGACGAC-3'

Reverse:
                                         (SEQ ID NO: 8)
5'-GTCGTCGAATGCAAGGGAGATTAAACCACCAAAGCAGCC-3'

Primers for mutation of Gly154 to Ser (G154S)
Forward:
                                         (SEQ ID NO: 9)
5'-GGCCCTCTCACCTTATCACTCACTGTGAATGATGATTTTTACG-3'

Reverse:
                                        (SEQ ID NO: 10)
5'-CGTAAAAATCATCATTCACAGTGAGTGATAAGGTGAGAGGGCC-3'

Primers for mutation of Glu180 to Ala (E180A)
Forward:
                                        (SEQ ID NO: 11)
5'-GAAGAACCCAACCATGCAGTCATGATCGTGGGTTATGG-3'

Reverse:
                                        (SEQ ID NO: 12)
5'-CCATAACCCACGATCATGACTGCATGGTTGGGTTCTTC-3'
```

Parental DNA inserted in pQE-30 (Qiagen, Calif.) as prepared in Example 2 was amplified using Pfu Ultra HF DNA polymerase with these primers for 16 cycles in a DNA thermal cycler (Perkin-Elmer). After digestion of the parental DNA with Dpn I, the amplified DNA with nucleotide substitution was incorporated and transformed into *E. coli* XL1-Blue (Stratagene). The mutations were verified by DNA sequencing. Double and triple point mutagenesis of A90I, G154S, and E180A were also done as described above. Each mutant plasmid was transformed into competent *E. coli* M15 (pREP4) cells (Qiagen). Each recombinant protein was individually expressed, purified and refolded as described above.

The substrate preferences of VX-4 were found to depend on AA residues occupying P2 site and thus, the diagnostic AA substitution might be relevant to the differential biochemistry of VX-4 compared to those of VX-2 and VX-3. Seven mutant forms of VX-4, in which these three AA residues were substituted by single, double, or triple site-directed mutagenesis (A90I, G154S, E180A, A90I/G154S, A90I/E180A, G154S/E180A, and A90I/G154S/E180A), were expressed in *E. coli*, and their proteolytic activities were examined as above. All of the refolded recombinant proteins showed hydrolytic activity against gelatin (FIG. 4(B)). Each mutant was expressed and analyzed by 12% SDS-PAGE (upper panel, FIG. 4(B), and by a gelatin substrate gel (lower panel, FIG. 4(B)).

The results of assays against peptide substrates are shown in FIG. 4(C). In assays against peptide substrates, all of the mutants harboring A901 and G154S by single or multiple substitutions maintained the pH-dependent substrate specificity of wild-type VX-4. Conversely, those containing E180A lost activity against Z-RR-MCA at pH 7.5 (FIG. 4(C)). The activities of wild-type and mutant VX-4s were assayed in 100 mM sodium acetate (pH 5.5) against Z-LR-MCA and 100 mM Tris-HCl (pH 7.5) against Z-RR-MCA at 37° C. In each case, 10 mM DTT was supplemented in reaction buffer. Maximal activity was presented as 100%. Mean±S.D. (n=3). These results demonstrate that Glu180 plays a key role in the pH-mediated switching of substrate specificity of VX-4.

The impact of a single AA substitution at a critical position has been shown in a *Leishmania major* cathepsin B-like protease, in which a Gly residue at the putative S2 pocket provided no detectable proteolytic activity against Z-RR-AMC, while its replacement with Glu restored activity. A similar result was also observed for papain, which exhibited a preference for Phe over Arg at the P2 position, but exhibited cathepsin B-like specificity when the S2 subsite was altered. A cathepsin B-like cysteine protease of *Giardia lamblia* that harbors a Glu residue at the S2 pocket was active against both Z-FR-MCA and Z-LR-MCA. The crystallographic structure of cruzain, an essential cysteine protease of *Trypanosoma cruzi*, demonstrated that the side chain of Glu205 might vary positions and interact with different substrates according to pH and availability of an electrostatically appropriate partner in the S2 pocket. Therefore, the S2 subsite might be intimately involved in the determination of ligand specificity. Although most of the residues delineating the S2 pocket are hydrophobic, a polar residue is present at the pocket's hollow end in some cysteine proteases including VX-4 (FIGS. 1A and 1B; see also above). The S2 pocket of these enzymes might retain a negative charge at physiologic pH, allowing the capability to bind the polar guanadino group of Arg at the P2 position.

Example 10

Immunocytochemical Staining and Visualizing the Localization in Cells

Thin blood smears (2 μl) were prepared from EDTA-containing venipuncture blood immediately after sampling from patients infected with *P. vivax* (gift from Dr. J S Yeom). A part of the slides were stained with 3% Giemsa, rinsed and air dried. The unstained thin films were treated with 3% $H_2O_2$ for 5 min and incubated with 1% bovine serum albumin. The films were incubated with mouse anti-rVX-4 antibody (1:500 dilutions in PBS). The reactions were visualized with an avidin-biotin complex (DAKO, Carpentaria, Calif.) and examined under a light microscope (Axiophot, Carl Zeiss).

The results reveal that VX-4 localizes densely within the food vacuoles and adjacent areas, as well as diffusely in the cytoplasm in erythrocytic Stages of *P. vivax*. The major hemoglobinases of *P. falciparum* (FP-2, FP-3 and plasmepsins) are targeted into a food vacuole through the ER-derived vesicles. However, it could not be clearly concluded whether the ER-derived, protease-containing vesicles are fuse with hemoglobin-containing transport vesicles, which were pinched off from cytosomes, or they directly contact with the food vacuole. However, investigations have been highly limited with the *P. vivax* proteins, not only due to low parasitemia in the patients' blood, but also due to failure of experimental maintenance of the parasite. The N-terminal regions of vavapains conserved the characteristic bipartite signal for trafficking to the food vacuole, which included cytoplasmic, transmembrane and lumenal motifs (FIGS. 1A and 1B). Alternatively, the proteolytic activities of VX-4 against erythrocytic actin and band-3 might suggest its additional role(s) in the remodeling of erythrocytic cytoskeleton, although the low activity with spectrin, which is one of the major cytoskeletal proteins in erythrocyte, makes it unclear (FIG. 5(D)).

The inventors prepared a mouse antiserum specific to rVX-4, which showed negligible cross-reactions with rVX-2 and rVX-3 as well as erythrocyte proteins, as shown in FIG. 6(A). FIG. 6(A) shows rVX-2, rVX-3 and rVX-4 proteins, which were separated by 12% SDS-PAGE and transferred to PVDF membrane. The membrane was incubated with ant-rVX-4 (1:1000 dilutions) for 4 h, with an additional incubation with peroxidase-conjugated anti-mouse IgG (1:2000 dilutions) for 4 h. The blot was developed using 4C1N chromogen.

The spatiotemporal expression pattern of VX-4 was also examined, and the results are shown in FIG. 6(B). In FIG. 6(B), a thin blood smear from a patient with vivax malaria was visualized by staining with anti-rVX-4 conjugated with avidin-biotin complex system. The protein was densely labeled in the food vacuoles and adjacent areas, as compared to the staining of the dark hemozoin pigment. As shown in FIG. 6(B), VX-4 was shown to be expressed through all of the intraerythrocytic stages of *P. vivax*, from ring to schizont/gametocyte stages. VX-4 localization appeared to be largely limited to the food vacuoles with dark homozoin pigment, while the protein was also labeled diffusely in the parasite cytoplasm. *P. falciparum* FP-3 seemed to have a biological implication(s), which is pivotal to the parasite's survival, in addition to the hemoglobin degradation and showed a distribution pattern similar to that of VX-4. Given the fact that VX-4 has hydrolytic activity against cytoskeletal proteins, the cytoplasmic distributions of VX-4 and FP-3 might suggest their cytosolic roles such as cytoskeletal remodeling and hemoglobin transportation, which is pivotal for the maintenance of intraerythrocytic stage of the parasites.

The substrate specificity of proteases depends largely on interactions between a substrate and the enzyme active site. The binding efficiency is greatly affected by the physicochemical micromilieu. The reaction pH may confer substrate preference, as has been seen with cruzain. The pH-dependent substrate switching of VX-4 might be relevant to its multiple biological roles; the protein might function as a maturase of *P. vivax* plasmepsin 4 in the plasma membrane or cytosomes at neutral pH, while it participates in the degradation of hemoglobin in the acidic food vacuole. VX-4 might also be involved in cytoskeletal remodeling for the invagination of parasite plasma membrane to form cytostomes and/or the hydrolysis of host proteins to facilitate parasite egress from the erythrocyte. VX-4 thus may be a multifunctional enzyme, performing pivotal functions to ensure parasite survival during the complex life cycle of *P. vivax*. Given the multifunctional activities of VX-4, which are critical for the survival and/or metabolic homeostasis of the parasite, the enzyme might be an attractive target for the development of new antimalarial chemotherapeutics. Work toward further identification of natural substrates and distinct protease functions are currently underway to facilitate a more comprehensive understanding of the biological significance of this enzyme.

REFERENCES CITED

All references cited herein are incorporated herein by reference in their entirety and for all purposes to the same extent as if each individual publication or patent or patent application was specifically and individually indicated to be incorporated by reference in its entirety for all purposes.

The discussion of references herein is intended merely to summarize the assertions made by their authors and no admission is made that any reference constitutes prior art. Applicants reserve the right to challenge the accuracy and pertinence of the cited references.

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatus within the scope of the invention, in addition to those enumerated herein will be apparent to those skilled in the art from the foregoing description. Such modifications and variations are intended to fall within the scope of the appended claims. The present invention is to be limited only by the terms of the appended claims, along with the full scope of equivalents to which such claims are entitled.

What is claimed is:

1. A cysteine protease, wherein the amino acid sequence of the cysteine protease is the amino acid sequence from SEQ ID NO: 1, and wherein glutamic acid at 180th position of SEQ ID NO: 2, which is a mature domain of SEQ ID NO: 1, is deleted, or substituted with an amino acid selected from the group consisting of arginine, histidine, lysine, alanine, isoleucine, leucine, methionine, phenylalanine, proline, tryptophane, valine, and cysteine.

2. The cysteine protease of claim 1, wherein the cysteine protease loses a degrading activity against a dipeptidyl substrate favored by cathepsin B at pH 6.6 to 9, wherein the dipeptidyl substrate has at least one hydrophilic amino acid.

3. The cysteine protease of claim 2, wherein the hydrophilic amino acid is selected from aspartic acid, glutamic acid, arginine, histidine, and lysine.

4. The cysteine protease of claim 2, wherein the dipeptidyl substrate is benzyloxycarbonyl-L-arginyl-L-arginine 4-methyl-coumaryl-7-amide.

5. A method of altering a substrate specificity of a cysteine protease according to claim 1, comprising deleting glutamic acid at 180th position of SEQ ID NO: 2, or substituting glutamic acid at 180th position of a mature domain of SEQ ID NO: 2 with an amino acid selected from the group consisting of arginine, histidine, lysine, alanine, isoleucine, leucine, methionine, phenylalanine, proline, tryptophane, valine, and cysteine, wherein the SEQ ID NO: 2 is a mature domain of SEQ ID NO: 1.

6. The method of claim 5, wherein a degrading activity against a dipeptidyl substrate is eliminated, wherein the dipeptidyl substrate is favored by cathepsin B at pH 6.6 to 9, and has at least one hydrophilic amino acid.

7. The method of claim 6, wherein the hydrophilic amino acid is selected from aspartic acid, glutamic acid, arginine, histidine, and lysine.

8. The method of claim 6, wherein the dipeptidyl substrate is benzyloxycarbonyl-L-arginyl-L-arginine 4-methyl-coumaryl-7-amide.

* * * * *

```
                        SEQUENCE LISTING

<160> NUMBER OF SEQ ID NOS: 12

<210> SEQ ID NO 1
<211> LENGTH: 484
<212> TYPE: PRT
<213> ORGANISM: Artificial Sequence
<220> FEATURE:
<223> OTHER INFORMATION: vivapain-4 from Plasmodium vivax

<400> SEQUENCE: 1

Met Glu Tyr His Met Glu Tyr Ser Asn Asp Lys Ser His Lys Pro Glu
  1               5                  10                  15

Lys Glu Leu Phe Val Glu Lys Ser Phe Gly Gly Arg Asn Gly Lys Gly
             20                  25                  30

Arg Lys Ser Leu Leu Val Val Leu Ser Val Ser Ala Met Cys Leu Leu
         35                  40                  45

Ala Gly Ser Ala Phe Tyr Phe Thr Arg Thr Gly Lys Gly Asn Asp Gly
     50                  55                  60

Pro Leu Tyr Gly Asn Ala Leu Asp Glu Ser Ser Ser Asp Asp Phe Ile
 65                  70                  75                  80

Ile Thr Ser Leu Leu Lys Ser Pro Gly Gly Lys Lys Phe Ile Val Ser
                 85                  90                  95

Lys Leu Gln Glu Leu Ile Ala Ser Tyr Asp Glu Asp Val Asn Ser Ala
            100                 105                 110

Lys Ala Ser Pro Ser Lys Glu Gly Pro Thr Gly Ala His Ser Thr Ser
        115                 120                 125

Val Ala Thr Val Ser Arg Gln Lys Gln Gly Asn Leu Lys Val Pro Lys
    130                 135                 140

Lys Ile Glu Ile Asn Phe Ala Asp Ser Arg Phe Leu Met Ile Asn Leu
145                 150                 155                 160

Glu Lys Val Asn Ala Phe Tyr Leu Phe Met Lys Glu His Gly Lys Lys
                165                 170                 175

Tyr Lys Thr Glu Glu Glu Met Gln Gln Arg Tyr Leu Ala Phe Thr Glu
            180                 185                 190

Asn Leu Ala Arg Ile Asn Ser His Asn Ser Lys Ala Asn Ile Leu Tyr
```

```
            195                 200                 205
Lys Lys Gly Thr Asn Gln Tyr Ser Asp Ile Ser Phe Glu Glu Phe Arg
    210                 215                 220

Lys Thr Met Leu Thr Leu Arg Phe Asp Leu Lys Lys Leu Ala Asn
225                 230                 235                 240

Ser Pro Tyr Val Ser Asn Tyr Asp Asp Val Leu Lys Lys Tyr Lys Pro
                245                 250                 255

Ala Asp Ala Val Val Asp Asn Glu Lys Tyr Asp Trp Arg Glu His Asn
            260                 265                 270

Ala Val Ser Glu Ile Lys Asn Gln Asn Leu Cys Gly Ser Cys Trp Ala
        275                 280                 285

Phe Gly Ala Val Gly Ala Val Glu Ser Gln Tyr Ala Ile Arg Lys Asn
    290                 295                 300

Gln His Val Leu Ile Ser Glu Gln Glu Leu Val Asp Cys Ser Asp Lys
305                 310                 315                 320

Asn Phe Gly Cys Phe Gly Gly Leu Ala Ser Leu Ala Phe Asp Asp Met
                325                 330                 335

Ile Asp Leu Gly Tyr Leu Cys Ser Glu Ser Asp Tyr Pro Tyr Val Gly
            340                 345                 350

Phe Lys Pro Arg Lys Cys Glu Ile Lys Cys Lys Glu Lys Tyr Thr
        355                 360                 365

Ile Lys Ser Tyr Val Lys Ile Pro Glu Glu Lys Tyr Lys Glu Ala Ile
    370                 375                 380

Gln Phe Leu Gly Pro Leu Thr Leu Gly Leu Thr Val Asn Asp Asp Phe
385                 390                 395                 400

Tyr Asp Tyr Lys Glu Gly Ile Phe Ser Ser Glu Cys Thr Glu Glu Pro
                405                 410                 415

Asn His Glu Val Met Ile Val Gly Tyr Gly Val Glu Glu Met Phe Asn
            420                 425                 430

Ser Glu Ser Asn Ala Ser Glu Lys His Tyr Tyr Tyr Ile Ile Lys Asn
        435                 440                 445

Ser Trp Gly Glu Asn Trp Gly Glu Lys Gly Phe Met Arg Ile Glu Thr
    450                 455                 460

Asp Glu Leu Gly Leu Gln Lys Thr Asn Asn Met Thr Glu Ala Tyr Val
465                 470                 475                 480

Pro Leu Leu Asp

<210> SEQ ID NO 2
<211> LENGTH: 245
<212> TYPE: PRT
<213> ORGANISM: Artificial Sequence
<220> FEATURE:
<223> OTHER INFORMATION: mature domain of vivapain-4 from Plasmodium
      vivax

<400> SEQUENCE: 2

Asn Ser Pro Tyr Val Ser Asn Tyr Asp Asp Val Leu Lys Lys Tyr Lys
1               5                   10                  15

Pro Ala Asp Ala Val Val Asp Asn Glu Lys Tyr Asp Trp Arg Glu His
            20                  25                  30

Asn Ala Val Ser Glu Ile Lys Asn Gln Asn Leu Cys Gly Ser Cys Trp
        35                  40                  45

Ala Phe Gly Ala Val Gly Ala Val Glu Ser Gln Tyr Ala Ile Arg Lys
    50                  55                  60

Asn Gln His Val Leu Ile Ser Glu Gln Glu Leu Val Asp Cys Ser Asp
```

```
                65                  70                  75                  80
Lys Asn Phe Gly Cys Phe Gly Gly Leu Ala Ser Leu Ala Phe Asp Asp
                    85                  90                  95

Met Ile Asp Leu Gly Tyr Leu Cys Ser Glu Ser Asp Tyr Pro Tyr Val
                100                 105                 110

Gly Phe Lys Pro Arg Lys Cys Glu Ile Lys Lys Cys Lys Glu Lys Tyr
            115                 120                 125

Thr Ile Lys Ser Tyr Val Lys Ile Pro Glu Gly Lys Tyr Lys Glu Ala
        130                 135                 140

Ile Gln Phe Leu Gly Pro Leu Thr Leu Gly Leu Thr Val Asn Asp Asp
145                 150                 155                 160

Phe Tyr Asp Tyr Lys Glu Gly Ile Phe Ser Ser Glu Cys Thr Glu Glu
                165                 170                 175

Pro Asn His Glu Val Met Ile Val Gly Tyr Gly Val Glu Glu Met Phe
            180                 185                 190

Asn Ser Glu Ser Asn Ala Ser Glu Lys His Tyr Tyr Tyr Ile Ile Lys
        195                 200                 205

Asn Ser Trp Gly Glu Asn Trp Gly Glu Lys Gly Phe Met Arg Ile Glu
210                 215                 220

Thr Asp Glu Leu Gly Leu Gln Lys Thr Asn Asn Met Thr Glu Ala Tyr
225                 230                 235                 240

Val Pro Leu Leu Asp
            245

<210> SEQ ID NO 3
<211> LENGTH: 27
<212> TYPE: DNA
<213> ORGANISM: Artificial Sequence
<220> FEATURE:
<223> OTHER INFORMATION: forward primer for amplifying the open reading
      frame of vivapain-4

<400> SEQUENCE: 3
atggaatatc acatggagta ctcgaac                                             27

<210> SEQ ID NO 4
<211> LENGTH: 27
<212> TYPE: DNA
<213> ORGANISM: Artificial Sequence
<220> FEATURE:
<223> OTHER INFORMATION: reverse primer for amplifying the open reading
      frame of vivapain-4

<400> SEQUENCE: 4
ctagtcaagc aggggacgt acgcctc                                              27

<210> SEQ ID NO 5
<211> LENGTH: 26
<212> TYPE: DNA
<213> ORGANISM: Artificial Sequence
<220> FEATURE:
<223> OTHER INFORMATION: primer containing a 5' Sac I site for preparing
      a recombinant vivapain-4

<400> SEQUENCE: 5
gagctcgaga tgcagcagag gtacct                                              26

<210> SEQ ID NO 6
<211> LENGTH: 26
<212> TYPE: DNA
<213> ORGANISM: Artificial Sequence
```

-continued

```
<220> FEATURE:
<223> OTHER INFORMATION: primer containing a 5' Pst I site for preparing
      a recombinant vivapain-4

<400> SEQUENCE: 6
ctgcagctaa tccacgagcg caacga                                          26

<210> SEQ ID NO 7
<211> LENGTH: 39
<212> TYPE: DNA
<213> ORGANISM: Artificial Sequence
<220> FEATURE:
<223> OTHER INFORMATION: forward primer for mutation of Ala90 to Ile
      (A90I)

<400> SEQUENCE: 7
ggctgctttg gtggtttaat ctcccttgca ttcgacgac                            39

<210> SEQ ID NO 8
<211> LENGTH: 39
<212> TYPE: DNA
<213> ORGANISM: Artificial Sequence
<220> FEATURE:
<223> OTHER INFORMATION: reverse primer for mutation of Ala90 to Ile
      (A90I)

<400> SEQUENCE: 8
gtcgtcgaat gcaagggaga ttaaaccacc aaagcagcc                            39

<210> SEQ ID NO 9
<211> LENGTH: 43
<212> TYPE: DNA
<213> ORGANISM: Artificial Sequence
<220> FEATURE:
<223> OTHER INFORMATION: forward primer for mutation of Gly154 to Ser
      (G154S)

<400> SEQUENCE: 9
ggccctctca ccttatcact cactgtgaat gatgattttt acg                       43

<210> SEQ ID NO 10
<211> LENGTH: 43
<212> TYPE: DNA
<213> ORGANISM: Artificial Sequence
<220> FEATURE:
<223> OTHER INFORMATION: reverse primer for mutation of Gly154 to Ser
      (G154S)

<400> SEQUENCE: 10
cgtaaaaatc atcattcaca gtgagtgata aggtgagagg gcc                       43

<210> SEQ ID NO 11
<211> LENGTH: 38
<212> TYPE: DNA
<213> ORGANISM: Artificial Sequence
<220> FEATURE:
<223> OTHER INFORMATION: forward primer for mutation of Glu180 to Ala
      (E180A)

<400> SEQUENCE: 11
gaagaaccca accatgcagt catgatcgtg ggttatgg                             38

<210> SEQ ID NO 12
<211> LENGTH: 38
<212> TYPE: DNA
<213> ORGANISM: Artificial Sequence
<220> FEATURE:
```

```
<223> OTHER INFORMATION: reverse primer for mutation of Glu180 to Ala
      (E180A)

<400> SEQUENCE: 12
ccataaccca cgatcatgac tgcatggttg ggttcttc                                  38
```